United States Patent
Cho

(10) Patent No.: US 7,955,815 B2
(45) Date of Patent: Jun. 7, 2011

(54) TWO-PHOTON FLUORESCENT PROBES FOR ACIDIC VESICLES IN LIVE CELLS AND TISSUE AND METHOD OF IMAGING ACIDIC VESICLES IN LIVE CELLS AND TISSUE USING THE SAME

(75) Inventor: Bong-Rae Cho, Seoul (KR)

(73) Assignee: Korea University Industrial & Academic Collaboration Foundation, Seoul (KR)

( * ) Notice: Subject to any disclaimer, the term of this patent is extended or adjusted under 35 U.S.C. 154(b) by 350 days.

(21) Appl. No.: 12/288,101

(22) Filed: Oct. 15, 2008

(65) Prior Publication Data
US 2009/0155837 A1 Jun. 18, 2009

(30) Foreign Application Priority Data

Dec. 18, 2007 (KR) .......................... 10-2007-0133747
Jun. 24, 2008 (KR) .......................... 10-2008-0059380

(51) Int. Cl.
*C12Q 1/02* (2006.01)
*G01N 21/77* (2006.01)
*G01N 21/76* (2006.01)

(52) U.S. Cl. ........................ 435/29; 564/169; 436/172
(58) Field of Classification Search .................... None
See application file for complete search history.

(56) References Cited

OTHER PUBLICATIONS

Zeng et al. Subcellular Localization of SIGMA-2 Receptors in Breast Cancer Cells Using Two-Photon and Confocal Microscopy; Cancer Research, vol. 67, No. 14 (2007) pp. 6708-6716.*
Kim et al. Two-Photon Fluorescent Probes for Acidic Vesicles in Live Cells and Tissue; Angew. Chem. Int. Ed., (2008) vol. 47, pp. 2231-2234.*
W. Denk, J. H. Strickler, W. W. Webb, *Science*, 1990, 248, 73.
W. R. Zipfel; R. M. Williams; W. W. Webb, *Nat. Biotechnol.* 2003, 21, 1369.
M. Goeppert-Mayer, *Ann, Phys.* 9 (1931) 273.
H. M. Kim, C. Jung, B. R. Kim, S.Y. Jung, J. H. Hong, Y.G. Ko, K. J. Lee, B. R. Cho, *Angew. Chem. Int. Ed.* 2007, 46, 3460-3463.
H. M. Kim, B. R. Kim, J. H. Hong, J.S. Park, K. J. Lee, Cho, B. R. *Angew. Chem. Int. Ed.* 2007, 46, 7445-7448.

* cited by examiner

*Primary Examiner* — Jon P Weber
*Assistant Examiner* — Paul C Martin
(74) *Attorney, Agent, or Firm* — Chirstie, Parker & Hale, LLP

(57) ABSTRACT

Provided are two-photon fluorescent probes for imaging acidic vesicles in live cells and tissue. The probes are represented by

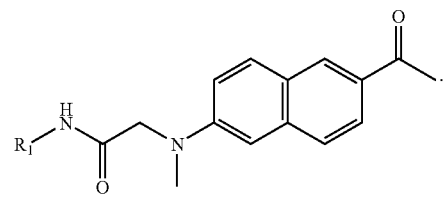

The probes can selectively bind to vesicles in cytosol to emit two-photon excited fluorescence with high intensity. Therefore, the use of the probes enables effective imaging of acidic vesicles. Further provided is a method for imaging acidic vesicles in live cells and tissue using the probes.

8 Claims, 18 Drawing Sheets
(12 of 18 Drawing Sheet(s) Filed in Color)

1a

1b

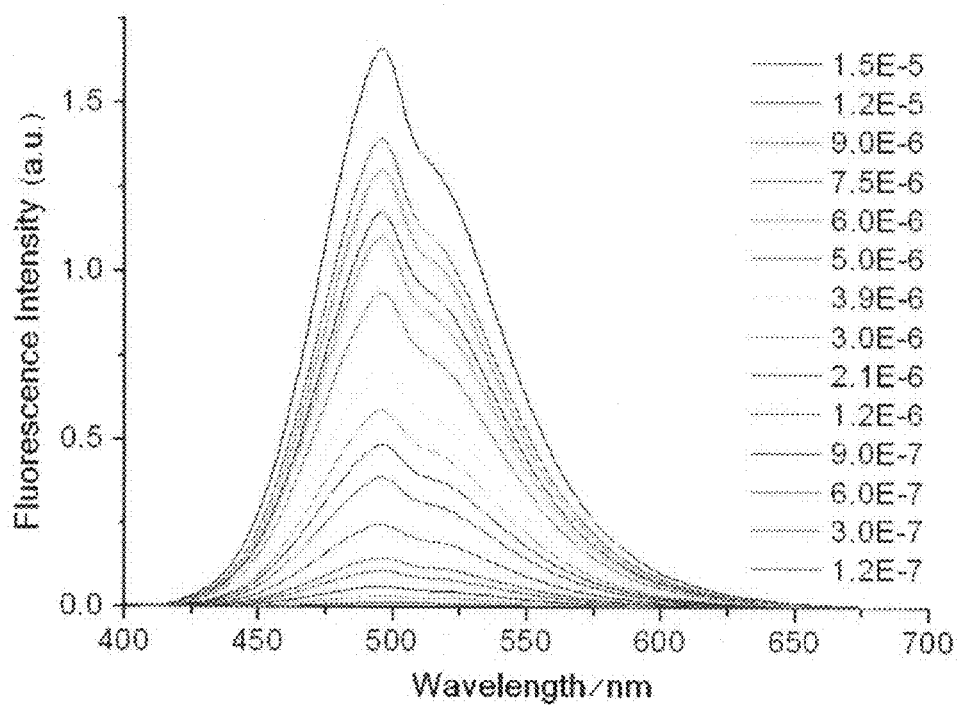
1c
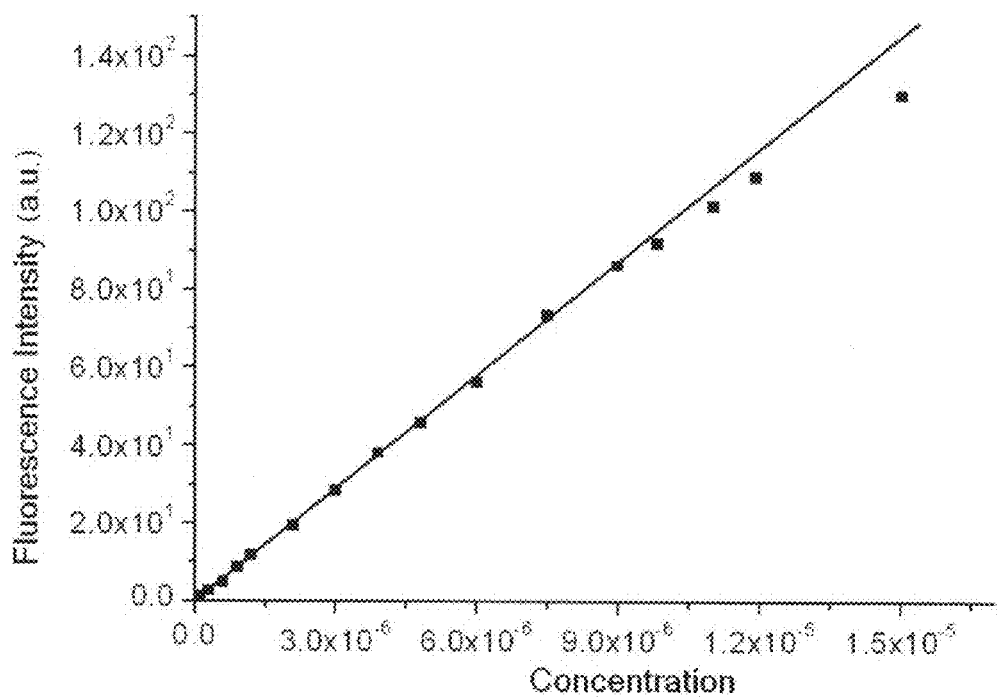
1d

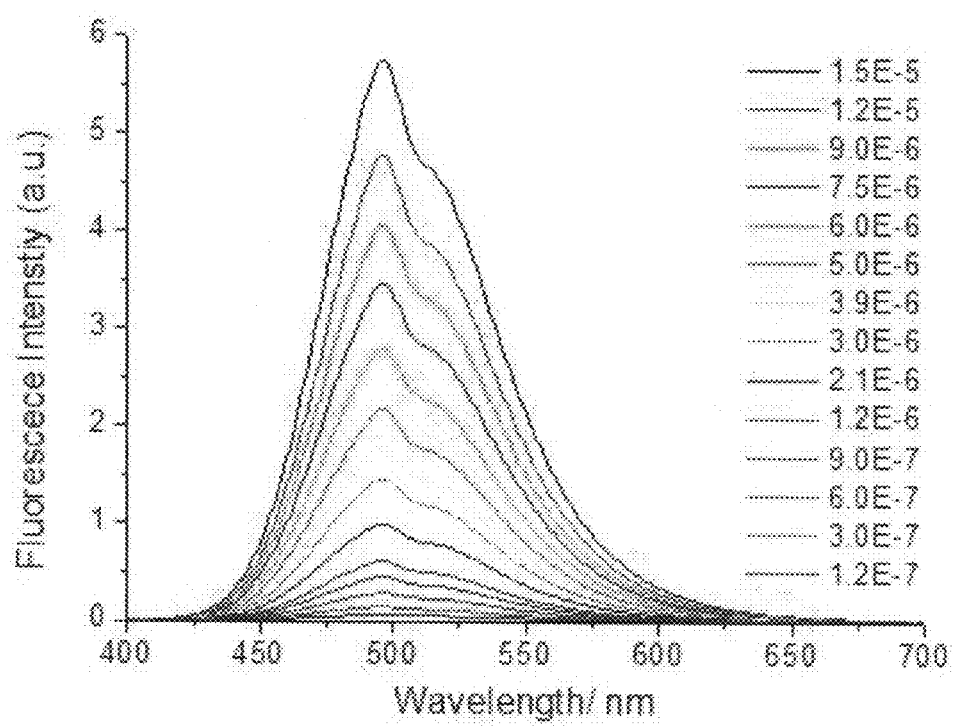
1e
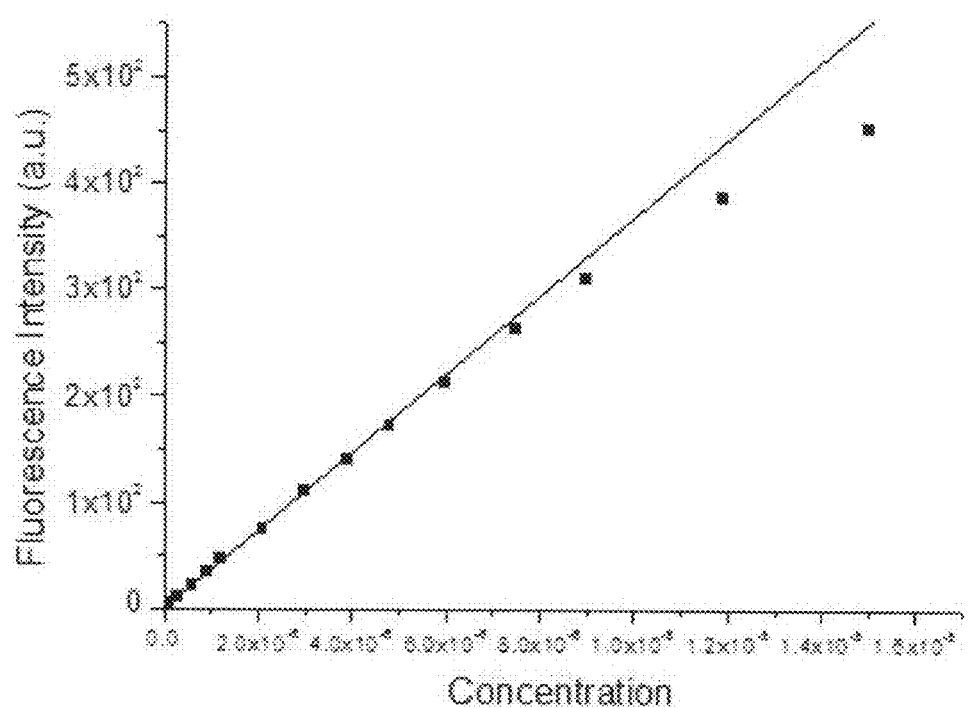
1f (Example 1)

2a (Example 2)

2b

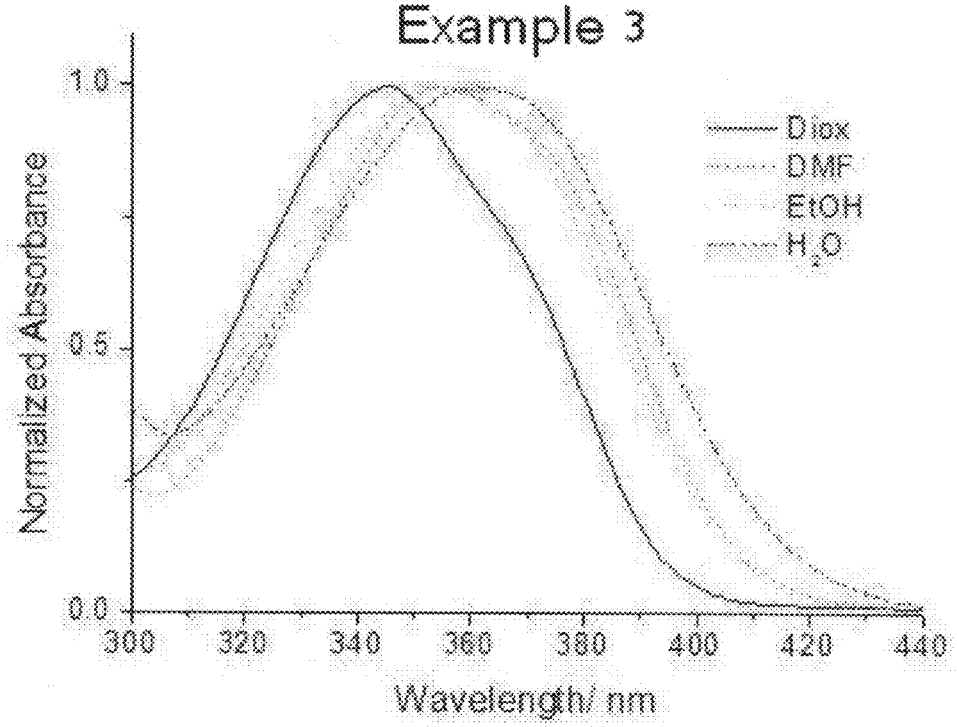
2c
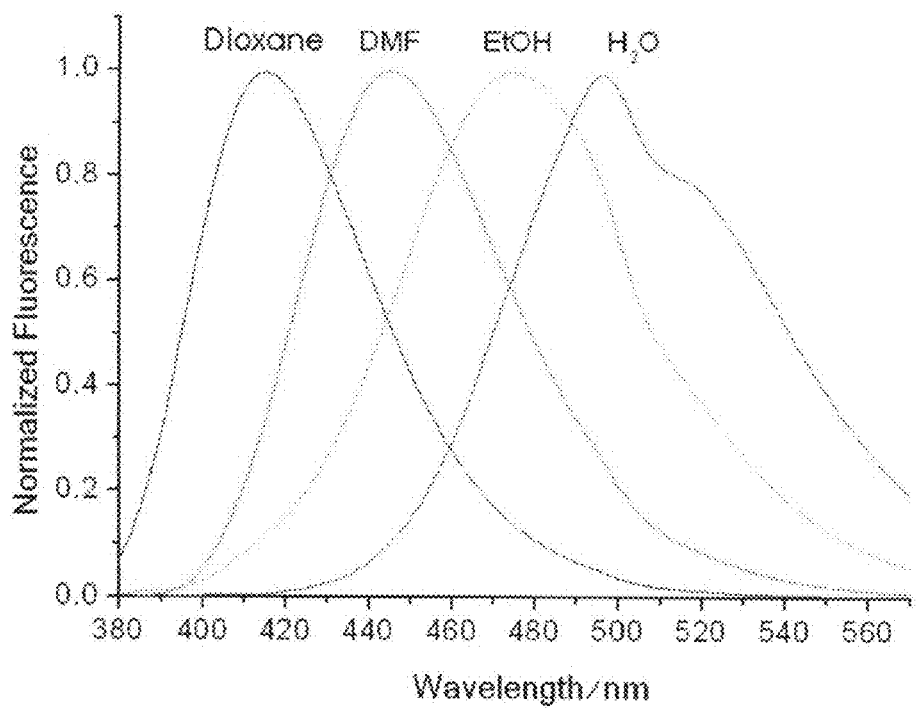
2d

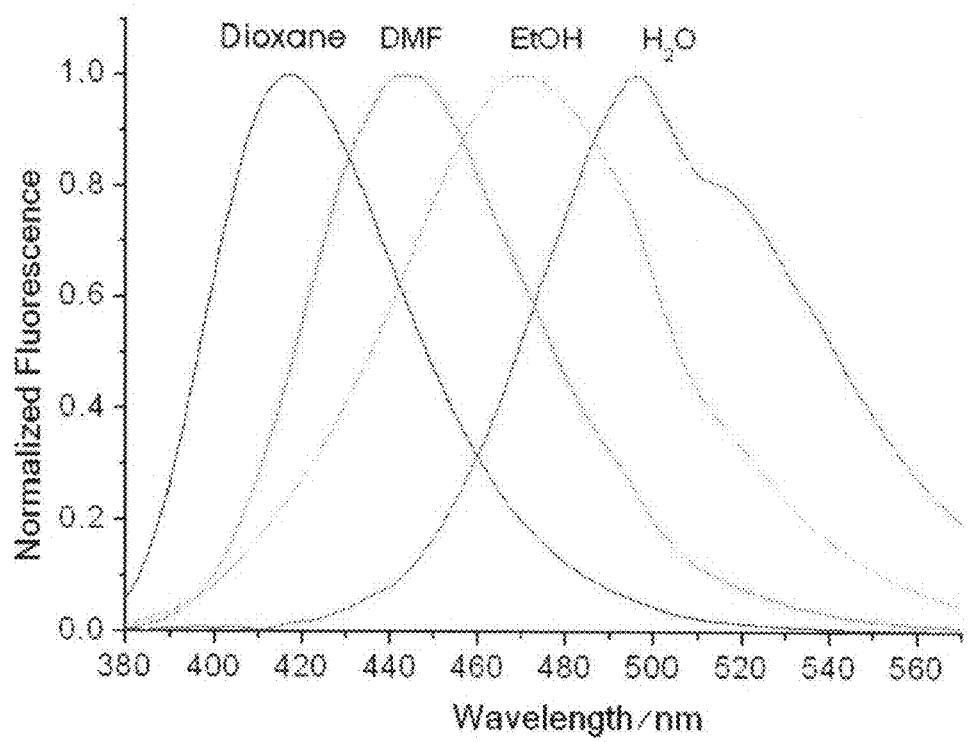
2e
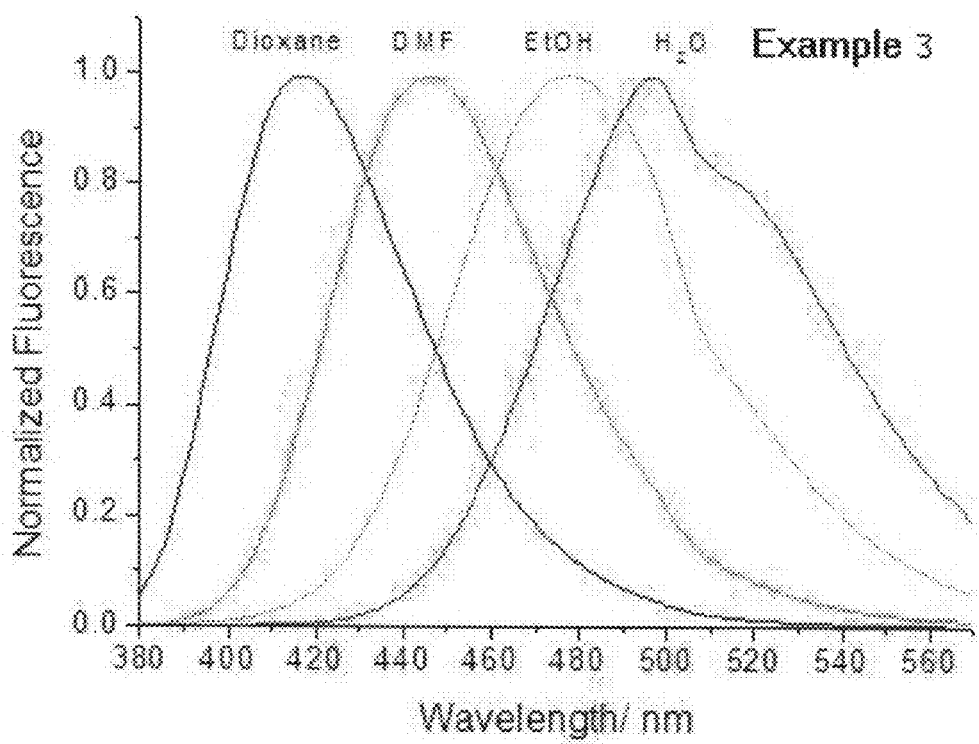
2f

3a

3b

3c

3d

4a

4b

4c

4d 5a
5b 5c
5d

6a

6b

6c 7a 7b

7c

8a

8b

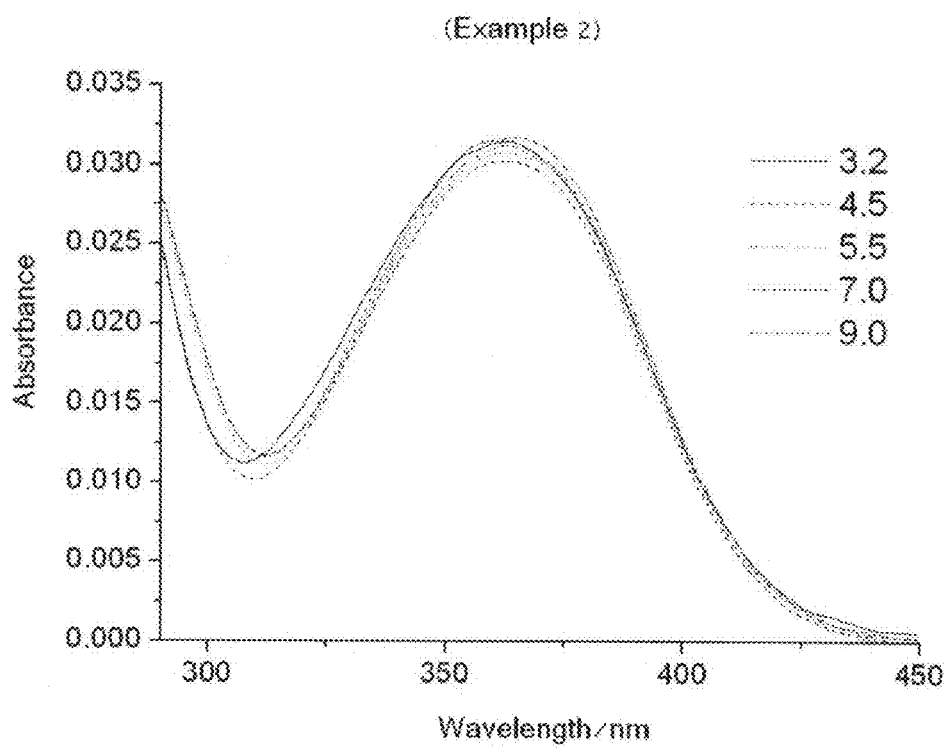
8c
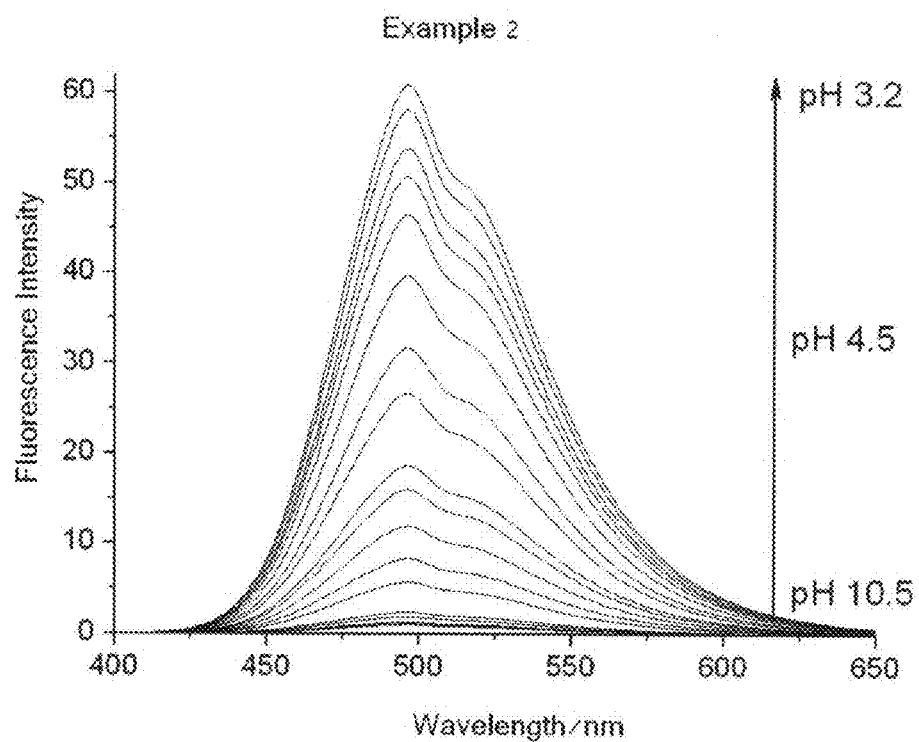
8d

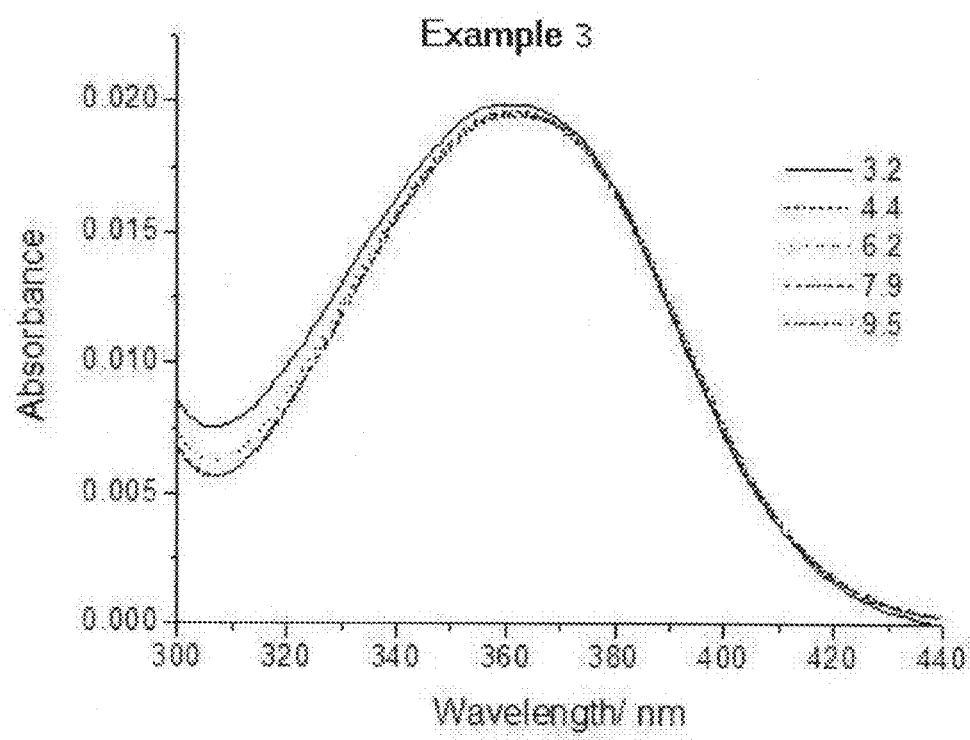
8e
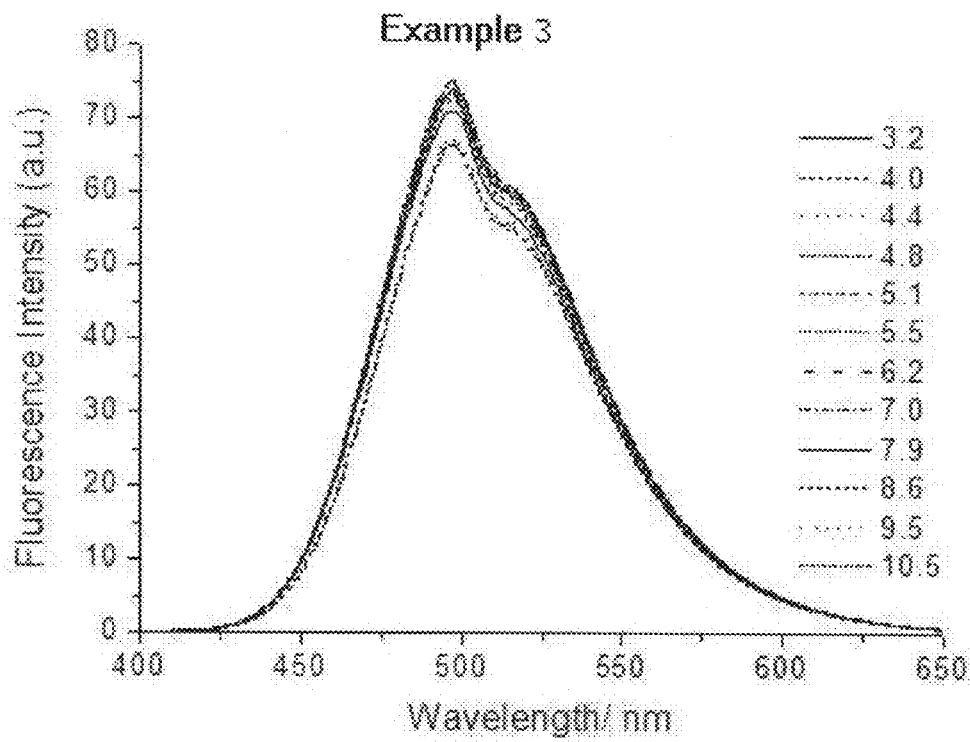
8f

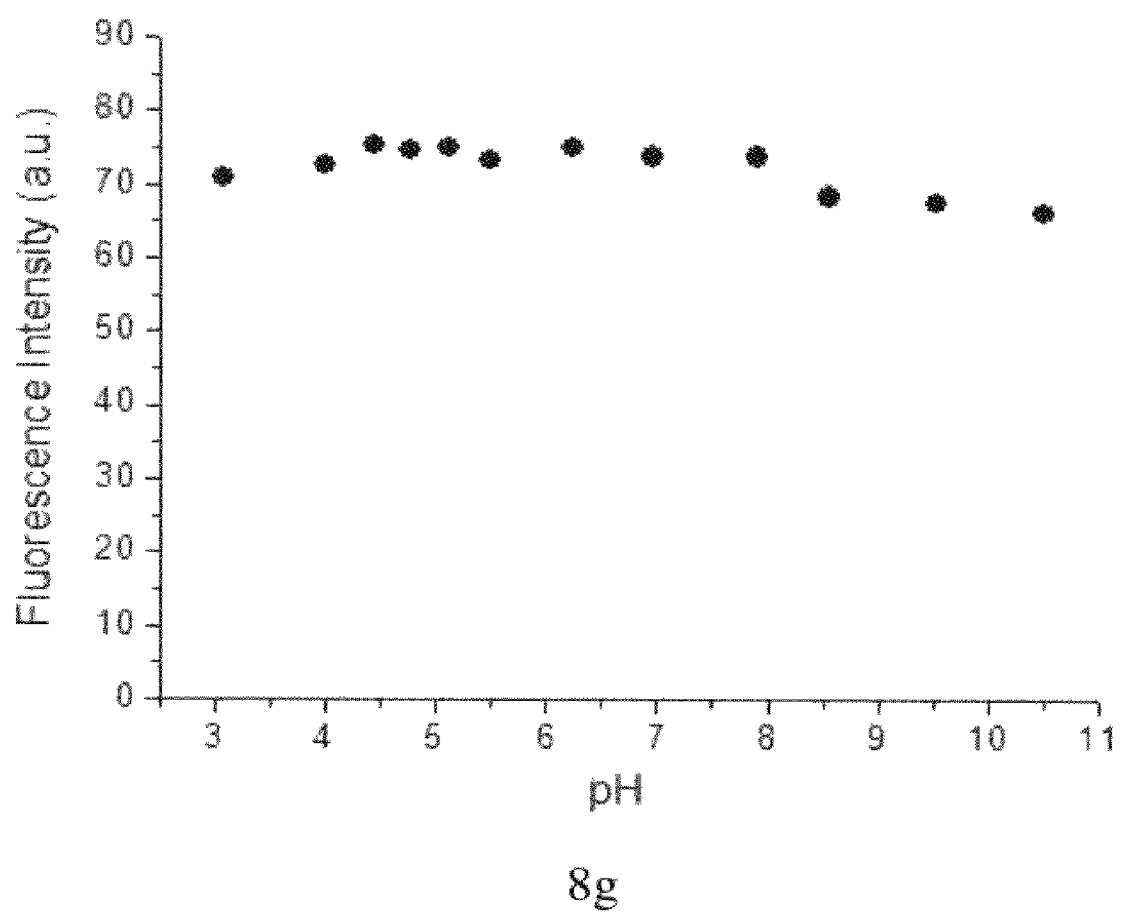
8g

11a

11b

TWO-PHOTON FLUORESCENT PROBES FOR ACIDIC VESICLES IN LIVE CELLS AND TISSUE AND METHOD OF IMAGING ACIDIC VESICLES IN LIVE CELLS AND TISSUE USING THE SAME

CROSS-REFERENCE TO RELATED APPLICATION

This application claims priority of Korean Patent Application Number 10-2007-0133747, filed on Dec. 18, 2007, and Korean Patent Application Number 10-2008-0059380, filed on Jun. 24, 2008.

BACKGROUND OF THE INVENTION

1. Field of the Invention

The present invention relates to two-photon fluorescent probes for imaging acidic vesicles in live cells and tissue and a method for imaging acidic vesicles in live cells and tissue using the two-photon fluorescent probes. More particularly, the present invention relates to two-photon fluorescent probes that have a large penetration depth and are selectively and clearly capable of visualizing vesicles under acidic conditions, and a method for imaging acidic vesicles in live cells and tissue using the two-photon fluorescent probes.

2. Description of the Related Art

Lysosomes and lysosome-related organelles constitute a system of acidic compartments (pH 4.0-5.0), which contain a large number of enzymes and secretory proteins exhibiting a variety of functions. To determine their functions, a variety of membrane-permeable fluorescent pH and lysosomal probes have been developed with some of them being commercially available.

However, use of these probes with one-photon microscopy (OPM) requires excitation with short-wavelength light (~350-550 nm) and presents several problems such as shallow penetration depth (<80 μm), photobleaching and cellular autofluorescence.

As an alternative method to solve the problems associated with the use of OPM, the use of two-photon microscopy (TPM) is considered.

TPM employs two near-infrared (NIR) photons for excitation and is of particular interest in tissue imaging (W. Denk, J. H. Strickler, W. W. Webb, *Science,* 1990, 248, 73.; W. R. Zipfel; R. M. Williams; W. W. Webb, *Nat. Biotechnol.* 2003, 21, 1369).

In 1932, Maria Goeppert-Mayer predicted a phenomenon in which two photons are spontaneously absorbed (*Ann, Phys.* 9 (1931) 273), but this two-photon excitation had not been practically utilized until strong laser sources were developed. Two-photon excitation is referred to as a phenomenon in which two photons are simultaneously absorbed in the same fluorophore having a sufficiently high photon density per unit volume and time by irradiation with a strong light source. The absorbed energy is the same as the sum of the energies of the two photons and the possibility of two-photon excitation is dependent on the square of the photon density.

Accordingly, the absorption of two photons is a secondary non-linear optical phenomenon. The photons in the excited state transit to the ground state and emit energy as fluorescence corresponding to the bandgap energy. This energy emission is called 'two-photon fluorescence'. It should be understood that the emitted photonic energy is greater than the photonic energy of an irradiation source. Substances emitting fluorescence by two-photon excitation are commonly termed 'two-photon probes'. Such two-photon probes may be excited by means of a light source capable of providing photonic energy corresponding to the bandgap energy. This excitation is referred to as 'one-photon excitation'. A fluorescence emission spectrum obtained by two-photon excitation has the same spectral properties as that obtained by one-photon excitation.

A first characteristic of two-photon excitation is that the excitation occurs only near the limited three-dimensional regions of light irradiators, and therefore, fluorescence emission obtained by the excitation is localized in three-dimensional space, resulting in a minimization of background fluorescence. A second characteristic of two-photon excitation is that the wavelength of the irradiated light is different from that of the emitted fluorescence. Particularly, the two-photon excitation is useful in observing small-volume samples because the excitation volume is very small.

Based on the above-mentioned characteristics, two-photon microscopy capable of inducing two-photon excitation by irradiation of light in the near-infrared region is currently in the spotlight in bioimaging applications. The reason for this is due to the following advantages: i) little damage of biomolecules by irradiation of near-infrared light, which enables the application of two-photon microscopy to living cells; ii) large penetration depth of near-infrared light; and iii) minimized tissue auto-fluorescence. Two-photon probes used for two-photon microscopy must satisfy the following requirements: i) large two-photon cross section ($\delta_{TPA}$) in the near-infrared region; ii) suitable water solubility, iii) high photostability; and iv) high binding selectivity for live cells and tissue.

However, most of fluorescent markers (two-photon fluorescent probes) presently used for TPM have small two-photon action cross sections ($\Phi\delta$) that limit their usage. Particularly, acidic conditions found in living cells and tissues extremely limit the efficiency of the conventional two-photon fluorescent probes. Two-photon fluorescent probes as effective markers that can visualize vesicles under acidic conditions have never been, to our knowledge, reported or developed.

An ideal two-photon fluorescent probe for staining acidic vesicles in cytosol selectively permeates the cytosol and stains vesicles without staining membranes dividing the cytosol to emit fluorescence. However, conventional two-photon fluorescent probes stain membranes as well as cytosol to cause the problem of mistargeting. Under these circumstances, there is an urgent need to develop two-photon fluorescent probes that can selectively stain vesicles in cytosol under acidic conditions to visualize the vesicles.

SUMMARY OF THE INVENTION

It is a first object of the present invention to provide two-photon fluorescent probes that can visualize acidic vesicles in live cells and tissue.

It is a second object of the present invention to provide a method for imaging acidic vesicles using the two-photon fluorescent probes.

In accordance with an aspect of the present invention, the first object can be accomplished by the provision of two-photon fluorescent probes for imaging acidic vesicles in live cells and tissue, represented by Formula 1:

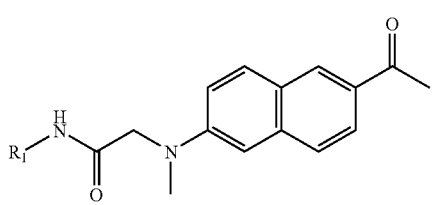

(1)

wherein $R_1$ is $(CH_3)_2NCH_2CH_2—$ or

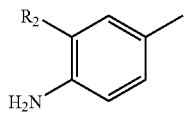

($R_2$ is a hydrogen atom or a methoxy group).

The two-photon fluorescent probes of the present invention can be excited by light with a wavelength of 780 nm, have two-photon action cross sections ($\Phi\delta$) of at least 86 GM, and show two-photon emission spectra whose fluorescence intensity increases with decreasing pH of cells to be visualized.

In addition, the two-photon fluorescent probes of the present invention show $pK_a$ values of 4 to 5 and have a water solubility of at least 5.0 μM. The absorption spectra of the two-photon fluorescent probes show bathochromic shifts with increasing solvent polarity. Furthermore, the two-photon fluorescent probes of the present invention can visualize acidic vesicles at a penetration depth of 250 μm.

In accordance with another aspect of the present invention, the second object can be accomplished by the provision of a method for imaging acidic vesicles in live cells and tissue, the method comprising introducing the two-photon fluorescent probe into cytosol to be visualized and observing two-photon excited fluorescence images emitted from the two-photon fluorescent probe.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

The above and other objects, features and other advantages of the present invention will be more clearly understood from the following detailed description taken in conjunction with the accompanying drawings, in which.

DETAILED DESCRIPTION OF THE INVENTION

Figure 1:
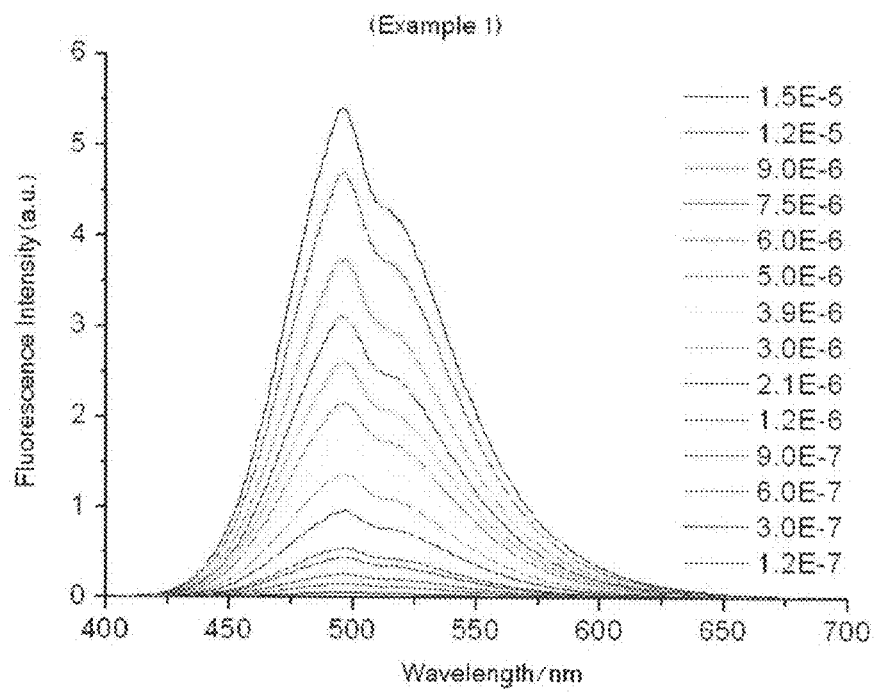
FIG. 1, including 1a-1f, shows plots of fluorescence intensity against the concentrations of two-photon fluorescent probes according to the present invention.
Figure 1:
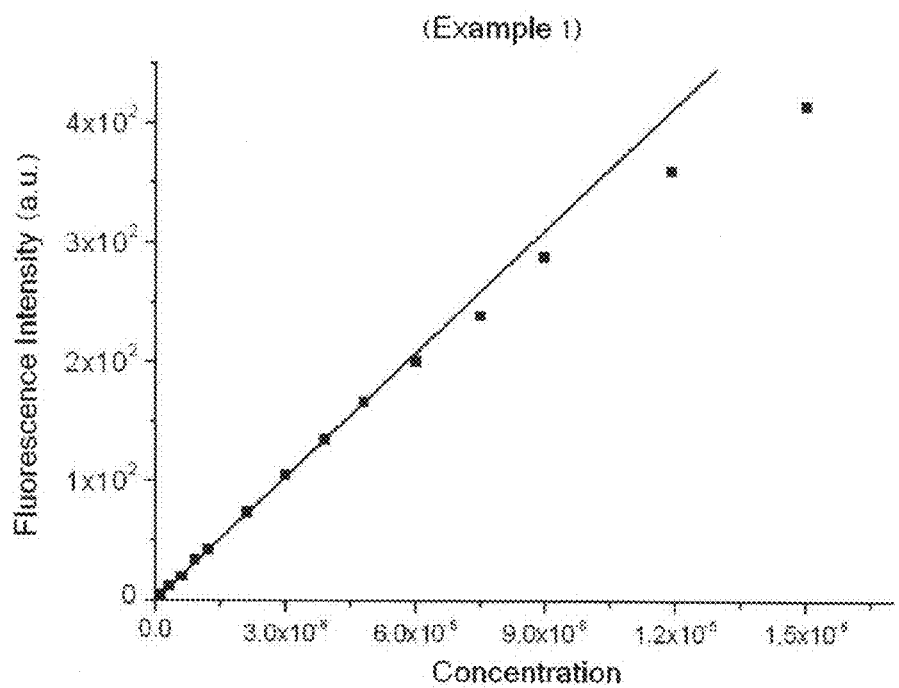

The present invention provides two-photon fluorescent probes for real-time imaging of vesicles in live cells or tissue under acidic conditions, represented by Formula 1:

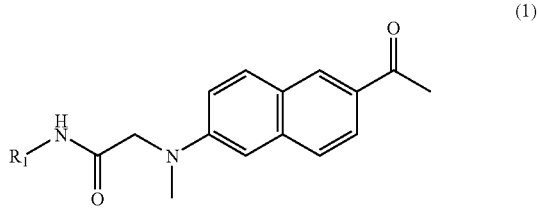

(1)

wherein $R_1$ is $(CH_3)_2NCH_2CH_2—$ or

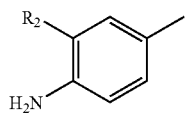

($R_2$ is a hydrogen atom or a methoxy group).

To design an efficient two-photon (TP) probe for acidic vesicles, the present inventors chose 2-acetyl-6-(dimethylamino)naphthalene ('acedan') as a fluorophore because acedan-derived TP probes for $Mg^{2+}$ and $Ca^{2+}$ exhibited significant TP action cross section, for the bright two-photon microscopy (TPM) image at low probe concentration, and high photostability, thus allowing the detection of the metal ions deep inside live cells for over 1,100 sec. The present inventors have introduced aniline and o-methoxy aniline ($pt_a$ ~4) or a tertiary amine ($pK_a$ ~10) as the proton binding site via the amide linkage to the fluorophore.

In particular embodiments, the two-photon fluorescent probes of the present invention may be the compounds of Formulae 2, 3 and 4:

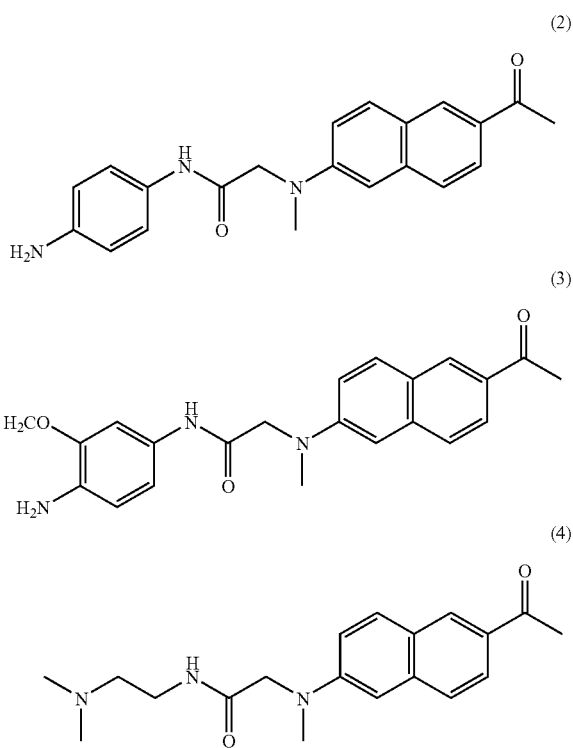

The two-photon fluorescent probes of Formulae 2 ('AH1') and 3 ('AH2') can be protonated at pH<4 to emit two-photon excited fluorescence (TPEF), whereas the two-photon fluorescent probe of Formula 4 ('AL1') can emit TPEF in acidic vesicles where it can be accumulated as the protonated form. In addition, these probes are capable of imaging acidic vesicles in living cells at >100 μm depth without mistargeting and photobleaching problems. Moreover, AL1 can visualize the transportation of acidic vesicles in the CA3 region for a long period of time with the use of two-photon microscopy (TPM). The effects of the two-photon fluorescent probes according to the present invention will be described in detail below.

As described above, the probes AH1 and AH2 of the present invention include aniline or its derivative as a proton binding site, where a proton ($H^+$) is bound under acidic conditions, thus allowing the probes to have emission spectra in the same wavelength band even under various pH conditions. Furthermore, the aniline (AH1) or o-methoxy-substituted aniline (AH2) structure providing a proton binding site undergoes photoinduced electron transfer to increase the two-photon fluorescence intensity of the compound, and as a result, more clear real-time images of acidic vesicles can be obtained.

Unlike conventional two-photon fluorescent probes, the two-photon fluorescent probes of the present invention selectively stain vesicles present in cytosol without staining membranes due to their relatively low molecular weights to emit clear fluorescence in the vesicles without any problems (e.g., mistargeting), thus allowing for imaging of the vesicles only.

The two-photon fluorescent probes AH1 and AH2 of the present invention have $pK_a$ values of 4 to 5, indicating that the equilibrium points of the fluorescence titration curves of the probes are created around pH 4.0. Accordingly, the two-photon fluorescent probes of the present invention can emit distinct and strong fluorescence under acidic conditions lower than pH 4.0.

The two-photon fluorescent probes of the present invention can be excited by light with a wavelength of 780 nm, whereas conventional fluorescent materials are excited by light in a wavelength band of 350 to 550 nm. That is, the excitation wavelength of the two-photon fluorescent probes according to the present invention is much longer than the excitation wavelengths of conventional fluorescent materials. Accordingly, the two-photon fluorescent probes of the present invention have a large penetration depth because of their long-wavelength excitation.

The two-photon fluorescent probes of the present invention have two-photon action cross sections (Φδ) of at least 86 GM when excited at 780 nm, which is a remarkably high level compared to the two-photon action cross sections (~10 GM) of conventional fluorescent materials, which will be explained in detail in the Example Section.

The two-photon fluorescent probes of the present invention show two-photon emission spectra whose fluorescence intensity increases with decreasing pH of cells to be visualized. Accordingly, as for vesicles at a low pH (pH 4-5), two-photon fluorescence images with very high fluorescence intensity can be obtained using the two-photon fluorescent probes of the present invention. In conclusion, the two-photon fluorescent probes of the present invention provide optimum conditions for real-time imaging of acidic vesicles.

Furthermore, the solubilities of the two-photon fluorescent probes according to the present invention are 5.0 μM or higher, which are sufficient to stain cells.

The absorption spectra of the two-photon fluorescent probes according to the present invention show bathochromic shifts with increasing solvent polarity, indicating shifts toward longer wavelengths under strongly acidic conditions and larger penetration depth of the probes, as explained above. This bathochromic shift is a characteristic that allows the two-photon fluorescent probes of the present invention to have a larger penetration depth under acidic conditions, i.e. highly polar conditions.

The present invention also provides a method for imaging acidic vesicles in live cells and tissue which comprises introducing the two-photon fluorescent probe into cytosol to be visualized and observing two-photon excited fluorescence images emitted from the two-photon fluorescent probe. In comparison with prior art methods, the imaging method of the present invention has advantages in that cells deep from the surface can be visualized and cells under acidic conditions can be visualized with high fluorescence intensity, thus enabling accurate monitoring of the cells.

Hereinafter, the present invention will be explained in more detail with reference to the following examples and the accompanying drawings. However, these examples serve to provide further appreciation of the invention but are not meant in any way to define or limit the scope of the invention.

EXAMPLES

Example 1

Preparation of Two-Photon Fluorescent Probe (AH1)

A mixture of 6-acetyl-2-[N-methyl-N-(carboxymethyl) amino]naphthalene (0.20 g, 0.78 mmol), N,N'-dicyclohexylcarbodiimide (0.18 g, 0.86 mmol), and 1-hydroxybenzotriazole (0.13 g, 0.94 mmol) in $CH_2Cl_2$ (20 mL) was stirred for 30 min. To this mixture, p-phenylenediamine.2HCl (0.50 g, 2.72 mmol) and $Et_3N$ (0.16 g, 1.56 mmol) in $CH_2Cl_2$ (5 mL) were added and stirred for 3 h under $N_2$. The resulting mixture was filtered and the filtrate was extracted with saturated $NaHCO_3$ (aq), dried over $Na_2SO_4$, filtered and concentrated in vacuo. The crude product was purified by column chromatography using $CHCl_3$/MeOH (10:1) as the eluent.

Yield: 0.13 g (47%); m.p.: 218° C.; $^1H$ NMR (300 MHz, $CDCl_3$): δ 8.37 (d, 1H, J=2 Hz), 8.04 (s, 1H), 7.99 (dd, 1H, J=9, J=2 Hz), 7.89 (d, 1H, J=9 Hz), 7.72 (d, 1H, J=9 Hz), 7.24 (d, 2H, J=9 Hz), 7.17 (dd, 1H, J=9, J=2 Hz), 7.07 (d, 1H, J=2 Hz), 6.64 (d, 2H, J=9 Hz), 4.12 (s, 2H), 3.62 (br s, 2H), 3.25 (s, 3H), 2.69 (s, 3H); $^{13}C$ NMR (100 MHz, DMSO $d_6$): δ 197.7, 167.8, 150.2, 145.6, 137.8, 131.3, 131.1, 130.8, 128.6, 126.6, 125.3, 124.7, 121.7, 116.9, 114.8, 114.4, 105.5, 56.0, 27.1 ppm; Anal. Calcd. for $C_{21}H_{21}N_3O_2$: C, 72.60; H, 6.09; N, 12.10. Found: C, 72.78; H, 6.21; N, 12.39.

Example 2

Preparation of Two-Photon Fluorescent Probe (AH2)

A mixture of 2-hydroxy-4-nitrophenylcarbamic acid tert-butyl ester (3.0 g, 11.8 mmol), which was prepared by the literature method, $K_2CO_3$ (2.5 g, 17.7 mmol), n-$Bu_4NI$ (0.87 g, 2.4 mmol), and MeI (1.8 g, 23.6 mmol) in dry acetone (50 mL) was refluxed for 20 h under $N_2$. The cooled reaction mixture was poured into 100 mL of water, collected by filtration, and washed with water (100 mL) and hexane (100 mL) to obtain an intermediate 1.

Yield: 2.5 g (80%); m.p. 117° C.; $^1H$ NMR (300 MHz, $CDCl_3$): δ 8.27 (d, 1H, J=9 Hz), 7.91 (dd, 1H, J=9, J=2 Hz), 7.73 (d, 1H, J=2 Hz) 7.36 (s, 1H), 3.98 (s, 3H), 1.54 (s, 9H); $^{13}C$ NMR (100 MHz, $CDCl_3$): δ 152.2, 147.0, 134.9, 118.3, 116.4, 105.5, 105.2, 81.9, 56.4, 28.6 ppm; Anal. Calcd. for $C_{12}H_{16}N_2O_5$: C, 53.73; H, 6.01; N, 10.44. Found: C, 53.98; H, 5.89; N, 10.59.

A mixture of the intermediate 1 and 10% Pd on carbon (0.16 g, 1.6 mmol) in ethanol (50 mL) was shaken under a hydrogen atmosphere for 5 h. The reaction mixture was filtered and washed with hot ethanol, and the solvent was removed in vacuo to obtain an intermediate 2.

Yield: 1.7 g (95%); $^1H$ NMR (300 MHz, DMSO $d_6$): δ 7.54 (s, 1H), 7.03 (d, J=9 Hz, 1H), 6.23 (d, 1H, J=2 Hz), 6.07 (dd, 1H, J=9, J=2 Hz), 4.93 (br s, 2H), 3.67 (s, 3H), 1.41 (s, 9H); $^{13}C$ NMR (100 MHz, DMSO $d_6$): δ 154.4, 147.3, 116.4, 106.0, 105.7, 98.6, 98.2, 78.7, 55.7, 28.7 ppm; Anal. Calcd. for $C_{12}H_{18}N_2O_3$: C, 60.49; H, 7.61; N, 11.76. Found: C, 60.88; H, 7.46; N, 11.78.

Next, an intermediate 3 was obtained in the same manner as in Example 1, except that the intermediate 2 was used instead of p-phenylenediamine. The intermediate 3 was dissolved in trifluoroacetic acid at 0° C. and the solution was stirred for 2 h. After the addition of toluene, the solution was evaporated to afford AH2.

Yield: 98%; m.p.: 157° C.; $^1H$ NMR (400 MHz, $CD_3OD$): δ 8.39 (d, 1H, J=2 Hz), 7.86 (dd, 1H, J=9, J=2 Hz), 7.85 (d, 1H, J=9 Hz), 7.65 (d, 1H, J=2 Hz), 7.64 (d, 1H, J=9 Hz), 7.28 (d, 1H, J=9 Hz), 7.24 (dd, 1H, J=9, J=2 Hz), 7.22 (dd, 1H, J=9, J=2 Hz), 7.01 (d, 1H, J=2 Hz), 4.34 (s, 2H), 3.92 (s, 3H), 3.32 (br s, 3.26 (s, 3H), 2.64 (s, 3H); $^{13}C$ NMR (100 MHz, DMSO $d_6$): δ 198.0, 168.8, 159.7, 159.5, 159.3, 159.0, 150.2, 137.8, 131.3, 131.1, 130.8, 126.6, 125.3, 124.6, 119.8, 116.8, 112.1, 105.5, 104.0, 56.7, 56.2, 27.0 ppm; Anal. Calcd. for $C_{22}H_{23}N_3O_3$: C, 70.01; H, 6.14; N, 11.13. Found: C, 70.18; H, 6.54; N, 11.03.

Example 3

Preparation of Two-Photon Fluorescent Probe (AL1)

A mixture of 6-acetyl-2-[N-methyl-N-(carboxymethyl) amino]naphthalene (0.20 g, 0.78 mmol), N,N'-dicyclohexylcarbodiimide (0.18 g, 0.86 mmol), and 1-hydroxybenzotriazole (0.13 g, 0.94 mmol) in $CH_2Cl_2$(20 mL) was stirred for 30 min. To this mixture, N,N-dimethylethylenediamine-2HCl (0.50 g, 2.72 mmol) and $Et_3N$ (0.16 g 1.56 mmol) in $CH_2Cl_2$ (5 mL) were added and stirred for 3 h under $N_2$. The resulting mixture was filtered and the filtrate was extracted with saturated $NaHCO_3$ (aq), dried over $Na_2SO_4$, filtered and concentrated in vacuo. The crude product was purified by column chromatography using $CHCl_3$/MeOH (10:1) as the eluent.

Yield: 47%; m.p.: 69° C.; $^1H$ NMR (400 MHz, $CDCl_3$): δ 8.34 (d, 1H, J=2 Hz), 7.96 (dd, 1H, J=9, J=2 Hz), 7.84 (d, 1H, J=9 Hz), 7.68 (d, 1H, J=9 Hz), 7.11 (dd, 1H, J=9, J=2 Hz), 6.96 (d, 1H, J=2 Hz), 6.92 (t, 1H, J=7 Hz), 4.05 (s, 2H), 3.35 (q, 2H, J=7 Hz), 3.18 (s, 3H), 2.68 (s, 3H), 2.34 (t, 2H, J=7 Hz), 2.05 (s, 6H); $^{13}C$ NMR (100 MHz, $CDCl_3$): δ 197.8, 169.8, 148.9, 137.3, 131.6, 131.0, 130.2, 126.5, 124.8, 116.2, 106.6, 58.0, 57.8, 45.0, 39.9, 36.6, 33.98, 26.5 ppm; Anal. Calcd. for $C_{19}H_{25}N_3O_2$: C, 69.70; H, 7.70 N, 12.83. Found: C, 69.78; H, 7.56; N, 12.77.

Experimental Example 1

Water Solubility

Each of the probes AH1, AH2 and AL1 prepared in Examples 1-3 was dissolved in DMSO to prepare a stock solution ($1.0 \times 10^{-3}$ M). The solution was diluted to $6.0 \times 10^{-3}$~$6.0 \times 10^{-5}$ M and added to a cuvette containing 3.0 mL of $H_2O$ by using a micro syringe. In all cases, the concentration of DMSO in $H_2O$ was maintained to be 0.2%. The fluorescence intensity of the probe was measured as a function of the probe concentration. FIG. 1 shows plots of fluorescence intensity against the concentrations of AH1 (1a, 1b), AH2 (1c, 1d) and AL1 (1e, 1f).

Referring to FIG. 1, the fluorescence intensities of the probes increased in all wavelength bands with increasing probe concentration.

The plots (1b, 1d and 1f) have a profile in which the fluorescence intensity increases with increasing probe concentration.

Referring to the profile, the fluorescence intensity increases linearly until the dye concentration reaches a predetermined level. Thereafter, the profile shows a slight downward curvature. The maximum concentration in the linear region was taken as the solubility. The solubilities of the probes AH1, AH2, and AL1 were 5.0, 9.0, and 5.0 μM, respectively. These results indicate that the probes are sufficiently soluble to stain cells.

Experimental Example 2

Figure 2:
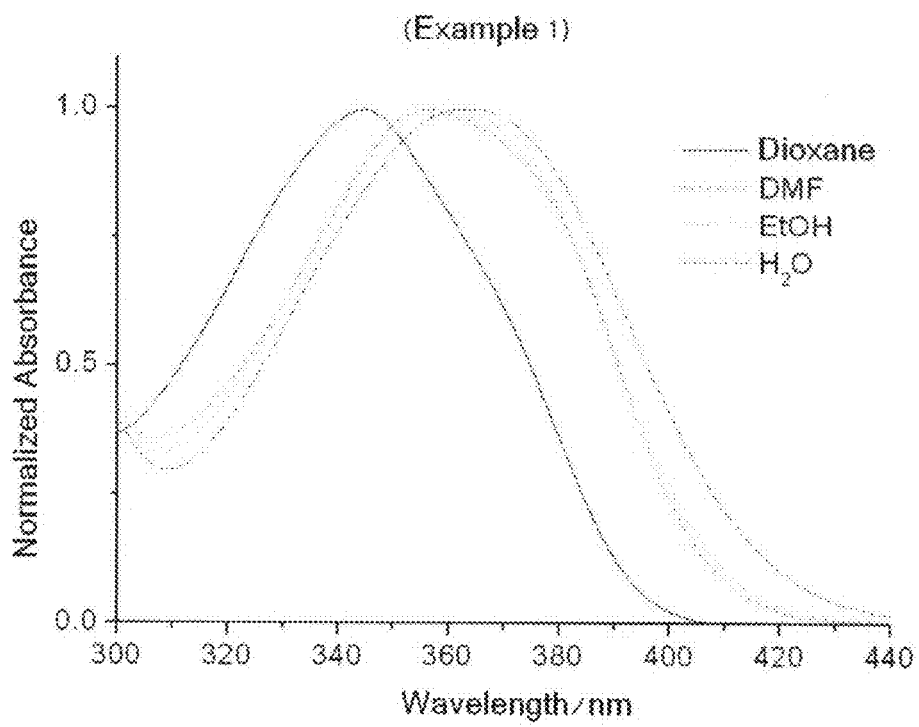
FIG. 2, including 2a-2f, shows absorption and emission spectra of two-photon fluorescent probes according to the present invention in 1,4-dioxane, DMF, EtOH, and H2O.
Figure 2:
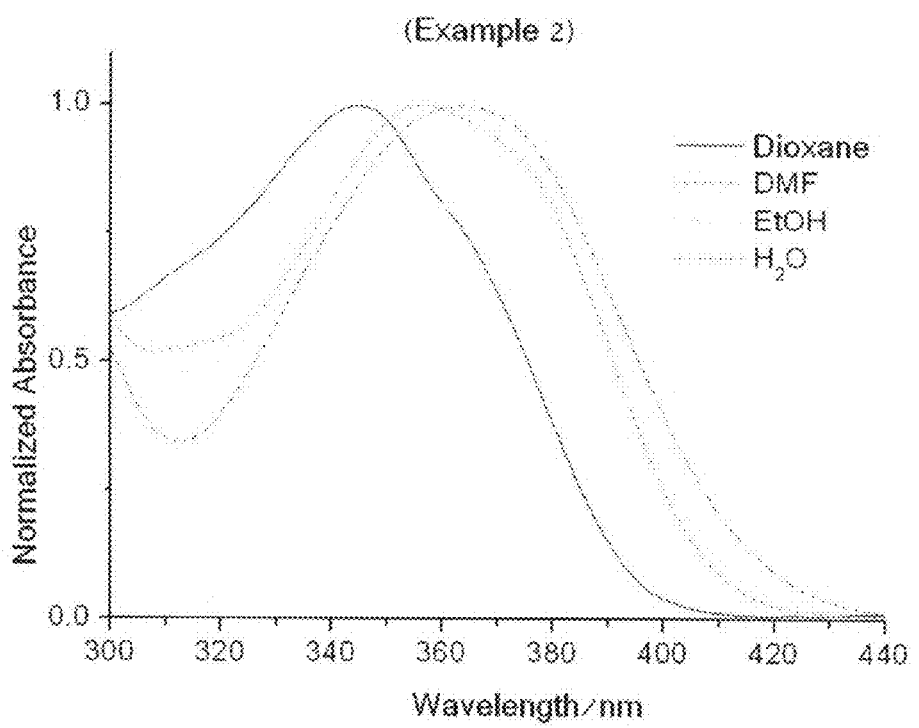

Analysis of Characteristics (Bathochromic Shifts) of the Two-Photon Fluorescent Probes with Solvent Polarity Absorption spectra of the probes AH1, AH2, and AL1 prepared in Examples 1-3 in 1,4-dioxane, DMF, EtOH and $H_2O$ as solvents were recorded on a Hewlett-Packard 8453 diode array spectrophotometer, and fluorescence spectra thereof were obtained under the same solvent conditions with an Amico-Bowman series 2 luminescence spectrometer. The results are shown in FIG. 2.

The absorption and fluorescence spectra of the probes showed bathochromic shifts with the solvent polarity in the order, $H_2O$>EtOH>DMF>1,4-dioxane, indicating that the probes can absorb light at long wavelengths and excited by the light under extreme polar conditions, such as acidic conditions.

Experimental Example 3

Two-Photon Microscope Images of Macrophages

Experimental Example 3-(1)

Figure 3:
FIG. 3, including 3a-3d, shows two-photon microscopy images of macrophages labeled with a two-photon fluorescent probe according to the present invention.
Figure 3:
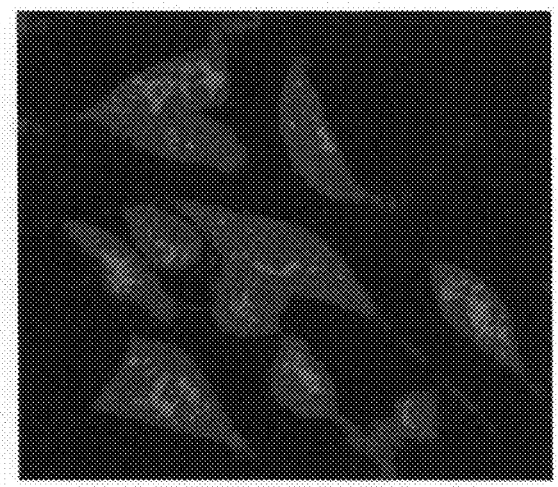
Figure 3:
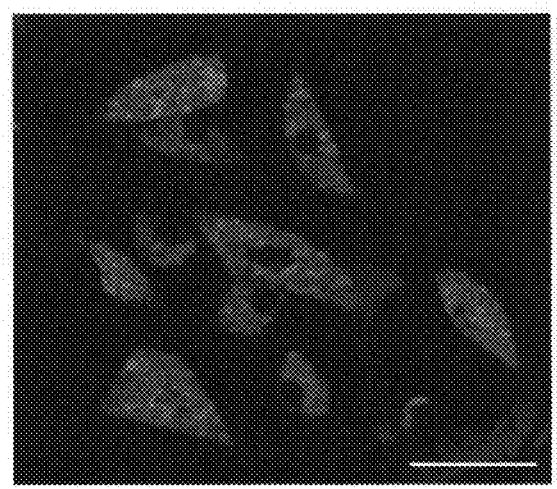
Figure 3:
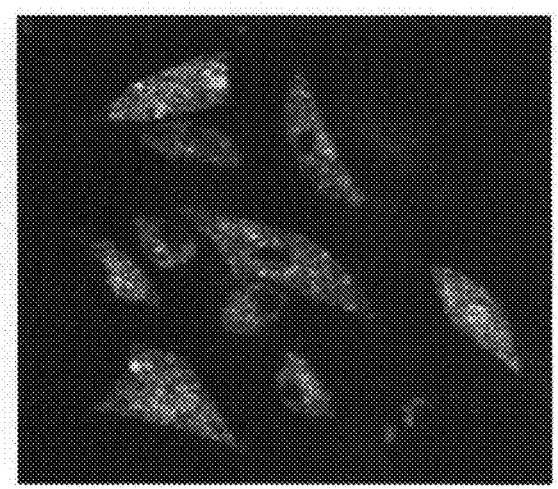

TPM images of individual macrophages labeled with the probe AH2 of Example 2 were obtained (FIG. 3).

It was previously reported that the TPM images of cytosol stained with two-photon fluorescent probes emitted two-photon excited fluorescence (TPEF) at 500-620 and 360-460 nm regions, which had been attributed to the probes associated with cytosol and membranes (H. M. Kim, C. Jung, B. R. Kim, S. Y. Jung, J. H. Hong, Y. G. Ko, K. J. Lee, B. R. Cho, *Angew. Chem. Int. Ed.* 2007, 46, 3460-3463; H. M. Kim, B. R. Kim, J. H. Hong, J. S. Park, K. J. Lee, Cho, B. R. *Angew. Chem. Int. Ed.* 2007, 46, 7445-7448). Since the conventional probes are partially bound to membranes and emit fluorescence, the problem of mistargeting is inevitably caused when it is intended to selectively visualize vesicles in cytosol using the probes, thus impeding accurate imaging of the vesicles.

In contrast, the TPM images of the AH2-labeled macrophages emitted TPEF only at 500-620 nm (3b), and not at 360-460 nm (3a), which was attributed to the membrane-bound probe.

To unambiguously determine whether the intense red spots (3b) are indeed the acidic vesicles, the macrophages were stained With LYSOTRACKER™ Red (LTR), a well known one-photon fluorescent probe, and a one-photon micrography (OPM) image thereof was obtained (3c). The TPM image was co-localized with the OPM image (3d). The two images (3b, 3c) were well merged, confirming that the probe AH2 is clearly capable of imaging the acidic vesicles.

Experimental Example 3-(2)

Acidic vesicles were imaged in the same manner as in Experimental Example 3-(1), except that the probe AH1 of Example 1 was used instead of the probe AH2 of Example 2. The results are shown in FIG. 4.

Figure 4:
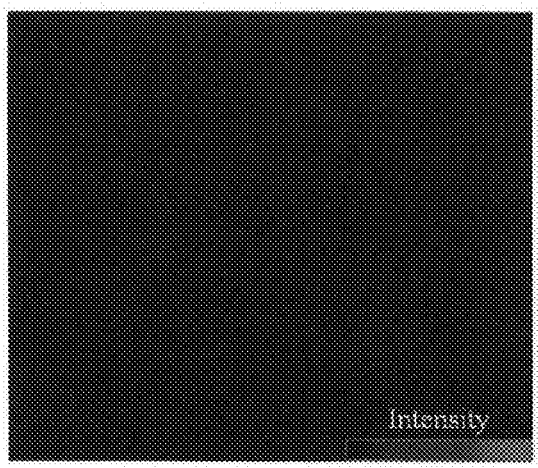
FIG. 4, including 4a-4d, shows two-photon microscopy images of macrophages labeled with another two-photon fluorescent probe according to the present invention.
Figure 4:
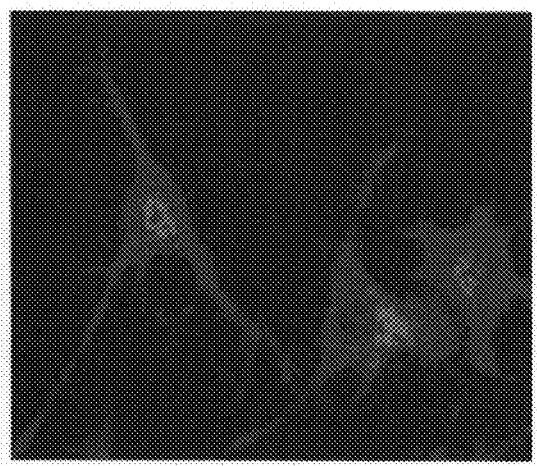
Figure 4:
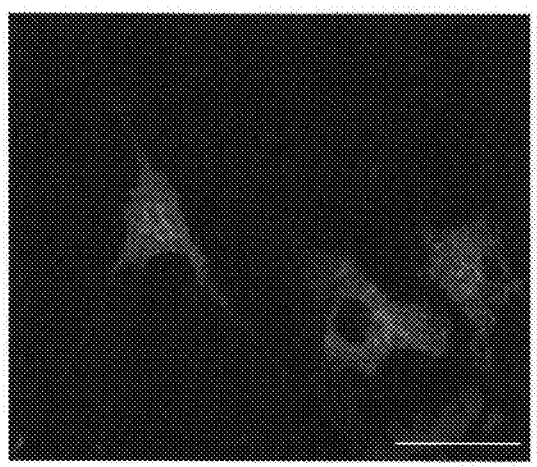
Figure 4:
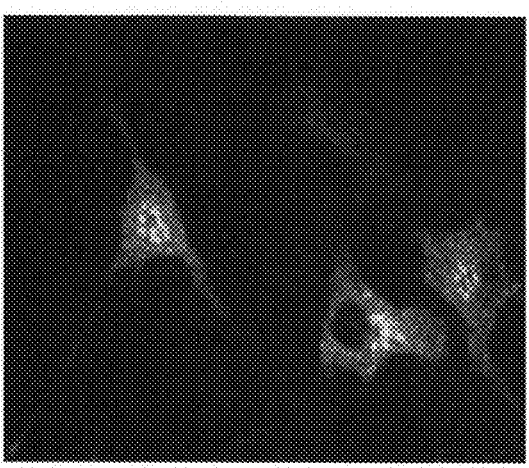

Referring to FIG. 4, the TPM images of the AH1-labeled macrophages emitted TPEF only at 500-620 nm (4b), and not at 360-460 nm (4a), which was attributed to the membrane-bound probe.

To unambiguously determine whether the intense red spots (4b) are indeed the acidic vesicles, the macrophages were stained with LTR and a one-photon micrography (OPM) image thereof was obtained (4c). The TPM image was co-localized with the OPM image (4d). The two images (4b, 4c) were well merged, confirming that the probe AH1 is clearly capable of imaging the acidic vesicles.

The fact that no TPEF image was obtained at 360-460 nm suggests that the probe was predominantly located in the cytosolic compartments and selectively imaged the acidic vesicles, presumably because the probe was introduced into the cytosol through the membranes due to its low molecular weight. As mentioned above, the probe accurately stains and visualizes acidic vesicles without mistargeting resulting from binding to and staining of membranes, so that a user can clearly monitor the acidic vesicles.

Experimental Example 3-(3)

Acidic vesicles were imaged in the same manner as in Experimental Example 3-(1), except that the probe AL1 of Example 3 was used instead of the probe AH2 of Example 2. The results are shown in FIG. 5.

Figure 5:
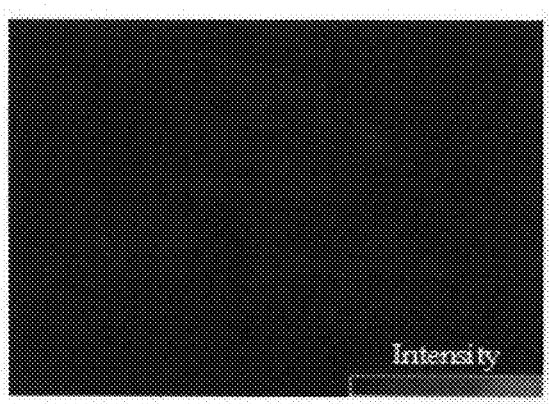
FIG. 5, including 5a-5d, shows two-photon microscopy images of macrophages labeled with another two-photon fluorescent probe according to the present invention.
Figure 5:
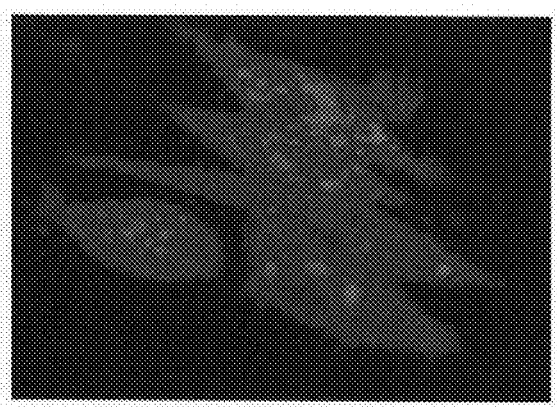
Figure 5:
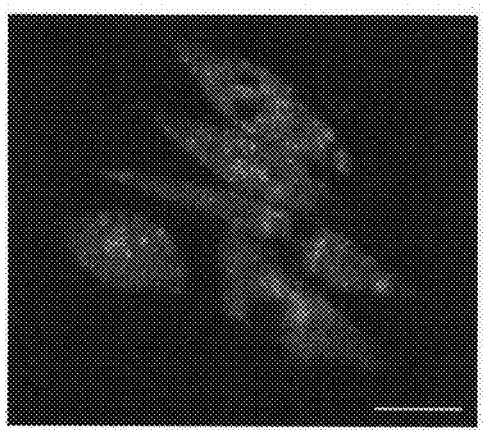
Figure 5:
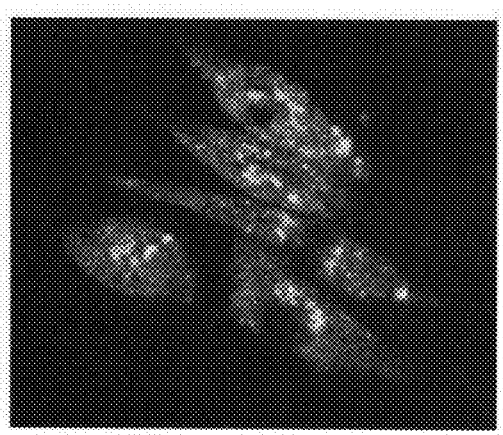

Referring to FIG. 5, the TPM images of the AL1-labeled macrophages emitted TPEF only at 500-620 nm (5b), and not at 360-460 nm (5a), which was attributed to the membrane-bound probe.

To unambiguously determine whether the intense red spots (5b) are indeed the acidic vesicles, the macrophages were stained with LTR and a one-photon micrography (OPM) image thereof was obtained (5c). The TPM image was co-localized with the OPM image (5d). The two images (5b, 5c) were well merged, confirming that the probe AL1 is clearly capable of imaging the acidic vesicles.

The fact that no TPEF image was obtained at 360-460 nm suggests that the probe was predominantly located in the cytosolic compartments and selectively imaged the acidic vesicles.

Experimental Example 4

Slices were prepared from the hippocampi of a 2-day-old rat. The hippocampal slices were cut into a thickness of 400 μm. The slices were incubated with the probes AH2 and AL1 (10-20 μM).

The slices were then washed and transferred to glass-bottomed dishes. The TPEF images of the slices were obtained.

Figure 6:
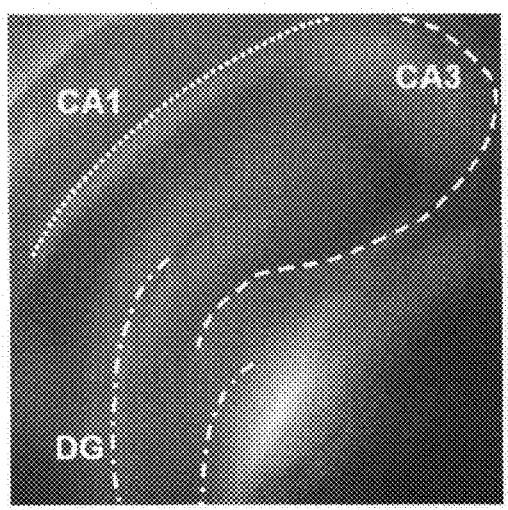
FIG. 6, including 6a-6c, shows two-photon excited fluorescence images obtained using a two-photon fluorescent probe of the present invention in Experimental Example 4.
Figure 6:
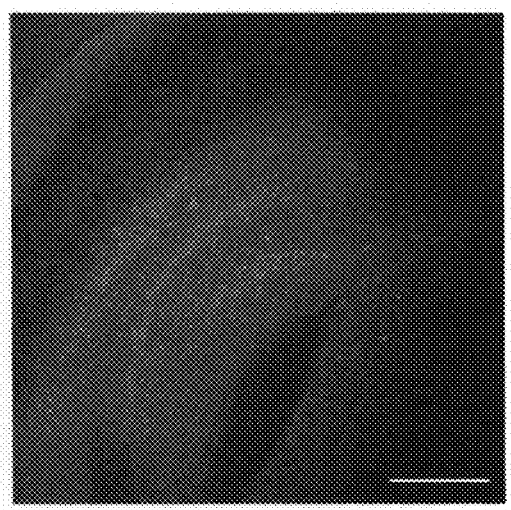
Figure 6:
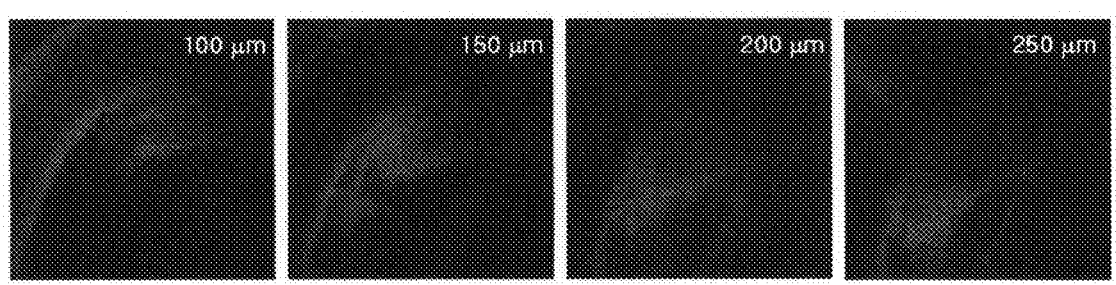

FIG. 6 shows TPEF images (6a, 6b) obtained using the probe AH2.

The bright field image (6a) shows the CA1 and CA3 regions as well as the dentate gyrus (DG) upon magnification 10×.

40 TPM images were accumulated along the z-direction at the depth of ~100-250 μm with magnification 10× (6b). The accumulated image reveals the average distribution of the acidic vesicles in the same regions.

TPM images were taken at depths of 100 to 250 μm (6c). That is, the use of the probe AH2 was effective in obtaining TPEF images of cells at a depth of 250 μm.

Figure 7:
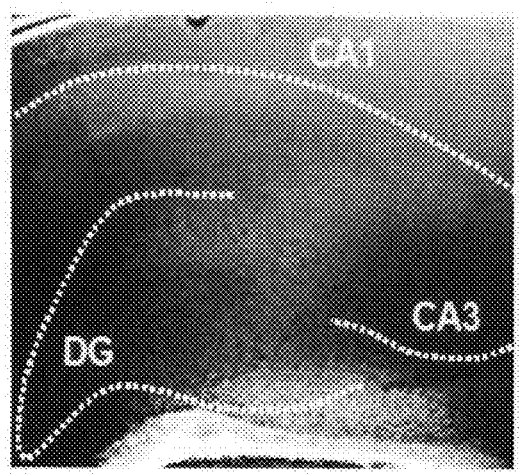
FIG. 7, including 7a-7c, shows two-photon excited fluorescence images obtained using another two-photon fluorescent probe of the present invention in Experimental Example 4.
Figure 7:
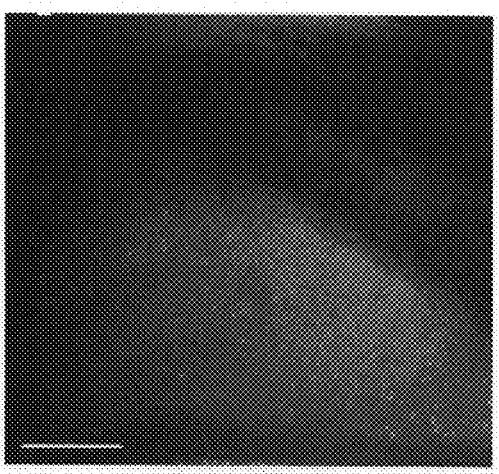
Figure 7:
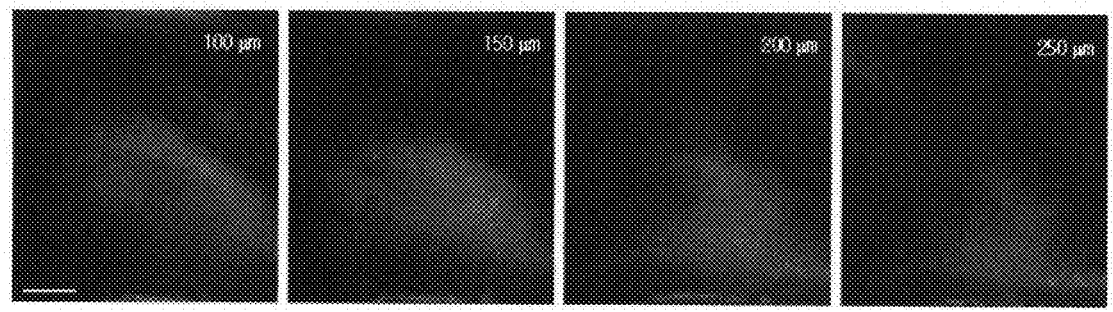

The same or similar results were obtained in the experiments of the probe AL1 (FIG. 7).

Experimental Example 5

Figure 8:
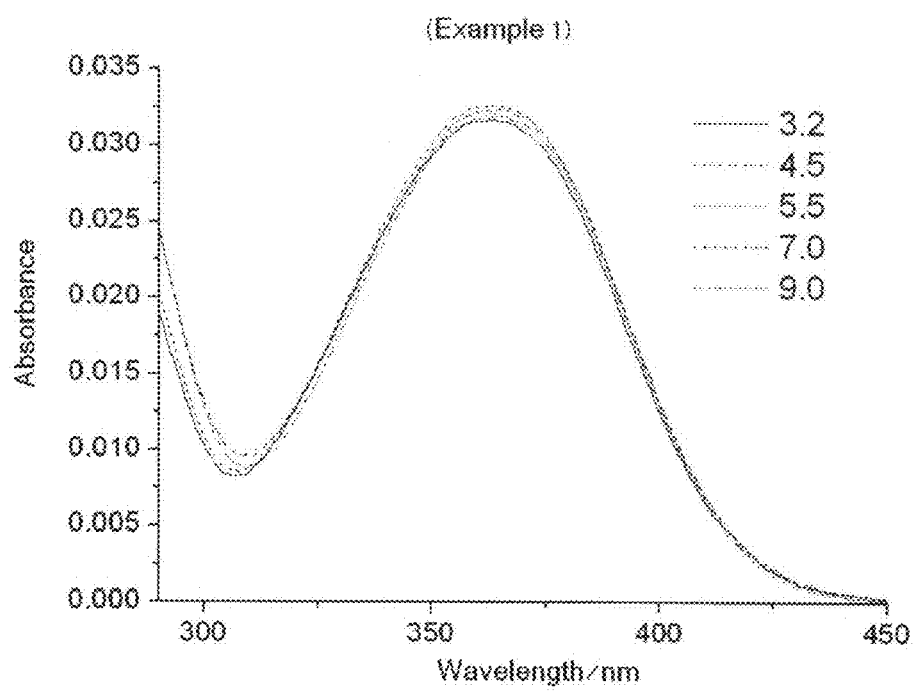
FIG. 8, including 8a-8g, shows one-photon absorption and emission spectra obtained using two-photon fluorescent probes of the present invention in Experimental Example 5.
Figure 8:
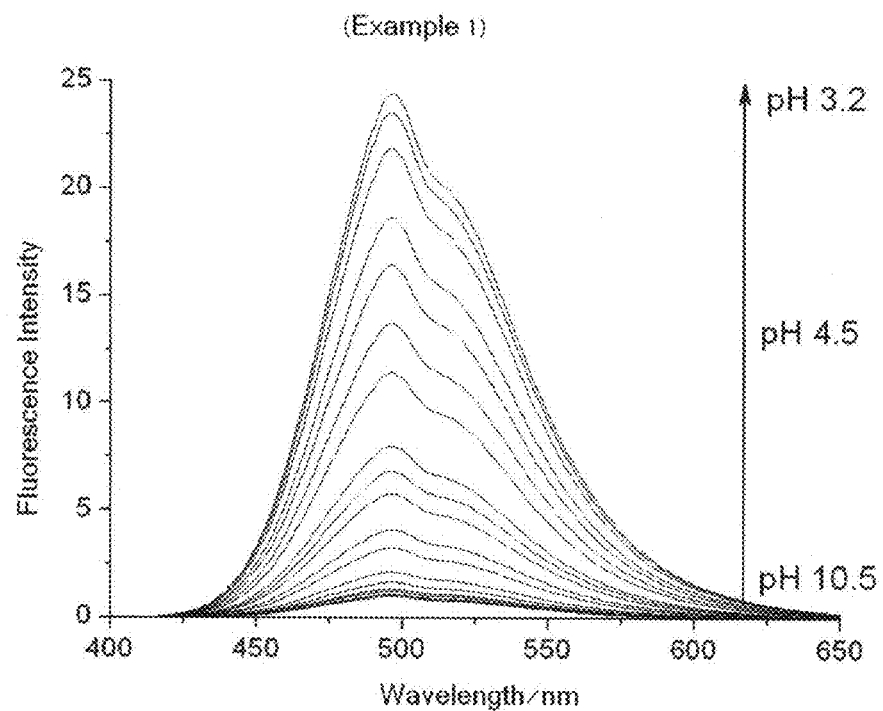

Analysis of Characteristics of the Two-Photon Fluorescent Probes as a Function of pH Each of the probes AH1 and AH2 was dissolved in a universal buffer solution (0.1 M citric acid, 0.1 M $KH_2PO_4$, 0.1 M $Na_2B_4O_7$, 0.1 M Tris, 0.1 M KCl 10 mM). The pH of the solution was gradually decreased, and one-photon absorption and emission spectra of the solution were obtained (FIG. 8).

The fluorescence intensity of the solution increased with decreasing pH without any change in the profile of the absorption spectrum. It is believed that the probe emitted fluorescence with strong intensity through a photoinduced electron-transfer (PET) process when the protonation of the probe proceeded under acidic conditions (pH<4).

One-photon absorption and emission spectra (8e, 8f, 8g) of the probe AL1 prepared in Example 3 reveal that the fluorescence intensity of the probe was maintained at a substantially constant level despite changes in acidity.

Figure 9:
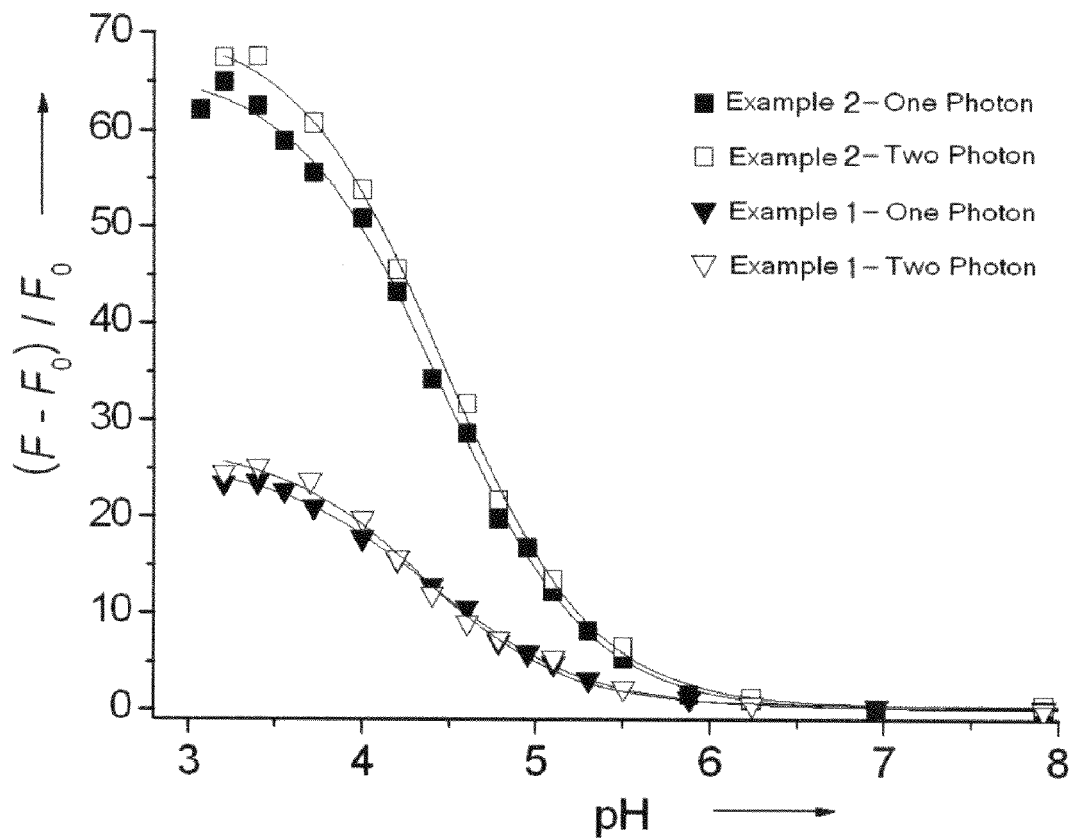
FIG. 9 shows fluorescence titration curves of two-photon fluorescent probes according to the present invention.

The fluorescence intensities of the probes AH1 and AH2 were measured, and titration curves thereof were plotted (FIG. 9). In FIG. 9, Y-axis represents the fluorescence intensity enhancement factor $[(F-F_o)/F_o]$ (F is the fluorescence intensity and $F_o$ is the minimum fluorescence intensity).

Referring to FIG. 9, the fluorescence intensities of the probes AH1 and AH2 increased dramatically around pH 4-5. The reason for the more dramatic change in the fluorescence intensity of the probe AH2 is possibly that the methoxy-substituted aniline generated greater photoinduced electron-transfer (PET) effect than the unsubstituted aniline. The difference in PET effect is attributed to a difference in the HOMO energy levels of the proton binding sites and the fluorophore, which will be explained more fully below.

Figure 10:
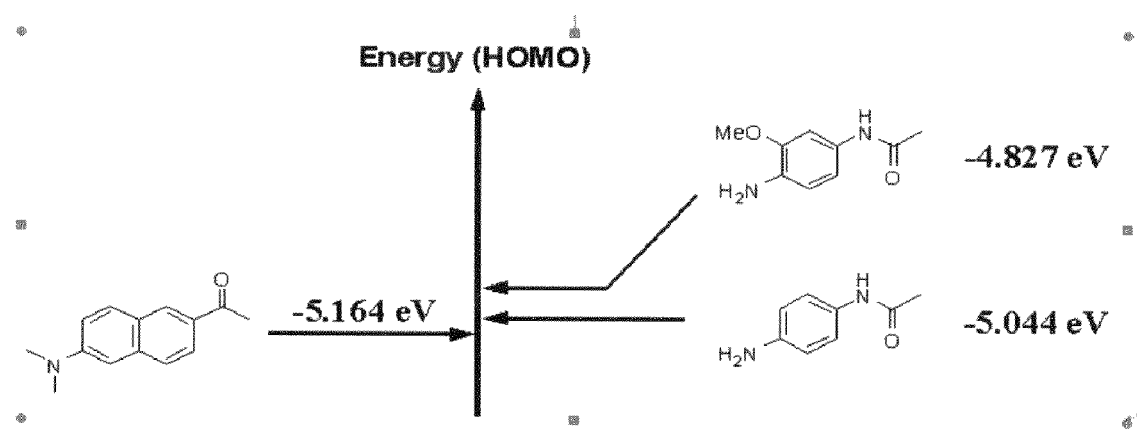
FIG. 10 shows HOMO energy levels of a fluorophore and different proton binding sites of two-photon fluorescent probes prepared in Examples 1 and 2.

FIG. 10 shows HOMO energy levels of the fluorophore and proton binding sites of the probes AH1 and AH2.

Referring to FIG. 10, the HOMO energy levels of the aniline having a methoxy group in the ortho-position and the unsubstituted aniline are −4.827 eV and −5.044 eV, respectively. The HOMO energy level of the fluorophore

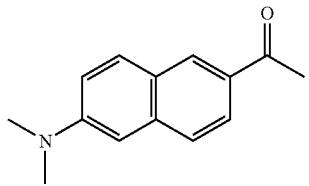

is −5.164 eV, which is closer to that of the unsubstituted aniline. Hence, the ortho-substituted aniline, whose HOMO energy level is higher than the fluorophore, is stabilized by protonation to emit a higher energy, which accounts for stronger fluorescence intensity.

Experimental Example 6

Analysis of Transportation of Acidic Vesicles

Figure 11:
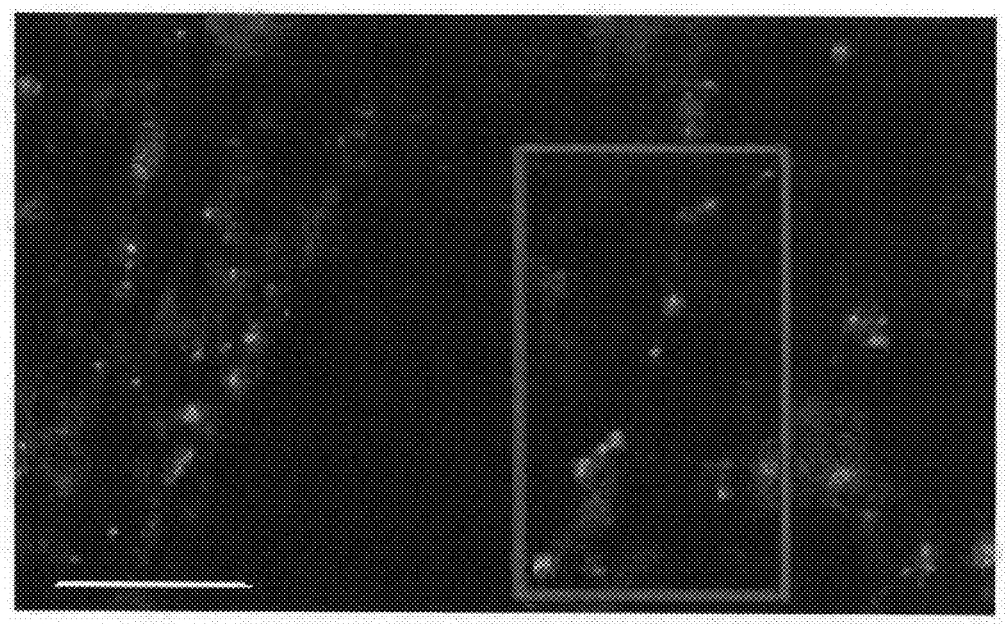
FIG. 11, including 11a-11b, shows images of an acute rat hippocampal slice stained with a two-photon fluorescent probe (10 μM) prepared in Example 3.
Figure 11:
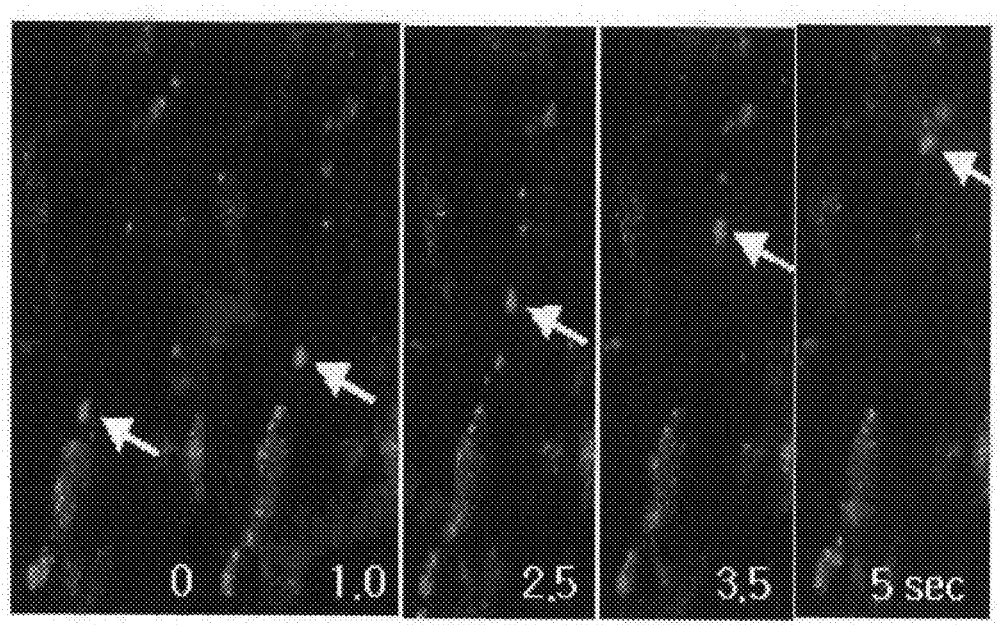

FIG. 11 shows images of an acute rat hippocampal slice stained with the probe (10 μM) of Example 3.

Specifically, FIG. 11 shows an image (11a) of CA3 regions at a depth of ~120 μm with magnification 100×, and enlarged images (11b) of a red box in 11a. The real time images (11b) for 5 sec reveal rapid transportations of the acidic vesicles between cell body and axon terminal along the axon, demonstrating that the probe is capable of imaging real-time change in the position of acidic vesicles.

Experimental Example 7 pK$_a$ Value Analysis

The pK$_a$ values were estimated from the fluorescence intensity measured as a function of the pH by using the relationship 1:

$$\log\left[(I_{max}-I)/(I-I_{min})\right]=\text{pH}-\text{pK}_a \quad (1)$$

wherein I represents the fluorescence intensity, and I$_{max}$ and I$_{min}$ represent the maximum and minimum fluorescence intensity, respectively.

The pK$_a$ values of the probes AH1 and AH2 calculated based on the measured fluorescence intensity are 4.42±0.03 and 4.18±0.01, respectively, implying that the inflection points (equilibrium points) of the fluorescence titration curves (FIG. 9) of the probes are around pH 4.0. These results demonstrate strong fluorescence intensity of the probes under acidic conditions (pH<4.0).

Experimental Example 8

Absorption of the Two-Photon Fluorescent Probes

Figure 12:
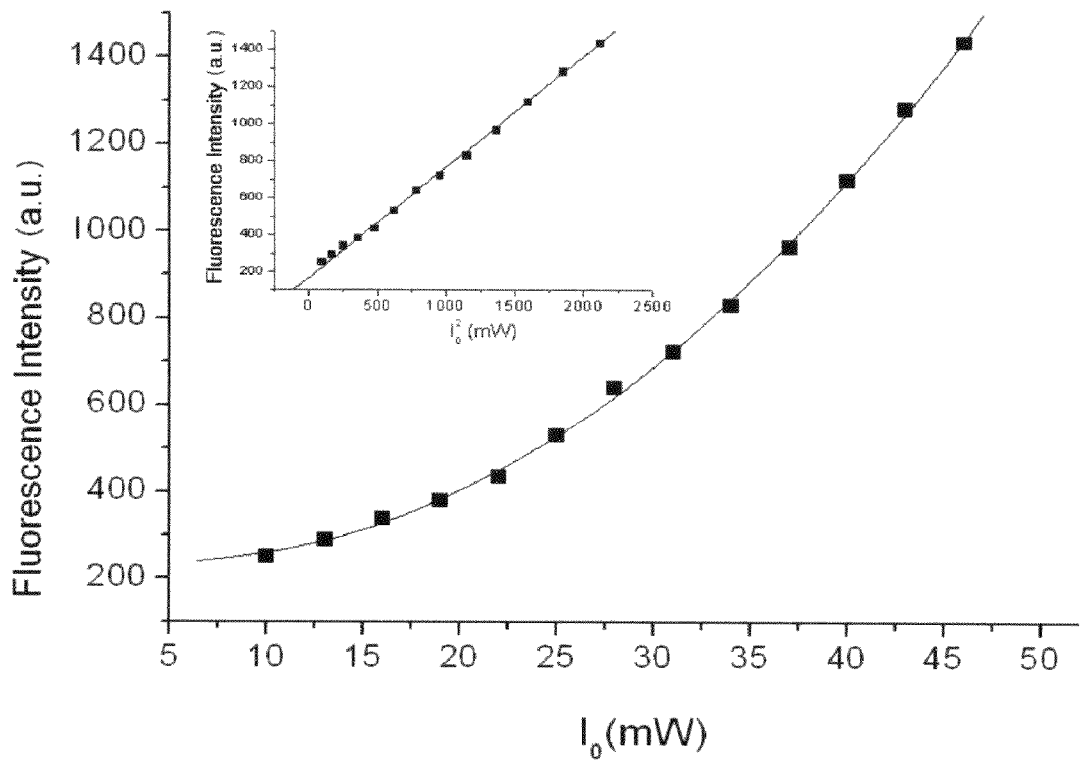
FIG. 12 shows fluorescence intensity of a two-photon fluorescent probe (5 μM) prepared in Example 2 in response to input laser power ($I_o$)

FIG. 12 shows fluorescence intensity of the probe AH2 (5 μM) in response to input laser power (I$_o$).

The plot of FIG. 12 showed a quadratic dependence of the fluorescence intensity of the probe on the input laser power, confirming the nonlinear absorption of the incident light in the probe. The small plot in FIG. 12 represents the relationship between the fluorescence intensity of the probe and the square of the input laser power (I$_o^2$), indicating that the fluorescence intensity of the probe is proportional to the square of the incident laser power.

Comparative Experimental Example 1

Measurements of Two-Photon Action Cross Section and Absorption Intensity

The two-photon cross section (δ) was determined by using femto second (fs) fluorescence measurement technique.

Specifically, each of the probes AH1, AH2, AL1 and LYSOTRACKER™ Red (DND-99) was dissolved in a universal buffer (pH=3.2) at a concentration of 5.0×10$^{-6}$ M and then the two-photon induced fluorescence intensity was measured at 740-940 nm by using fluorescein (8.0×10$^{-6}$ M, pH=11) as the reference, whose two-photon property has been well characterized.

The intensities of the two-photon induced fluorescence spectra of the reference and the sample probe were measured, and the two-photon cross section of the sample probe was calculated according to Equation 2:

$$\delta = \frac{S_s \Phi_r \phi_r c_r}{S_r \Phi_s \phi_s c_s} \delta_r \quad (2)$$

wherein the subscripts s and r represent the sample probe and the reference, respectively, δ represents the two-photon cross section of the sample probe, and S represents the intensity of the signal collected by a detector, Φ represents the fluorescence quantum yield, φ represents the overall fluorescence collection efficiency of the experimental apparatus, c represents the number density of the molecules in solution, and δ$_r$ represents the two-photon cross section of the reference.

The two-photon action cross section of the sample probe was calculated by multiplying the two-photon cross section by the quantum yield.

Figure 13:
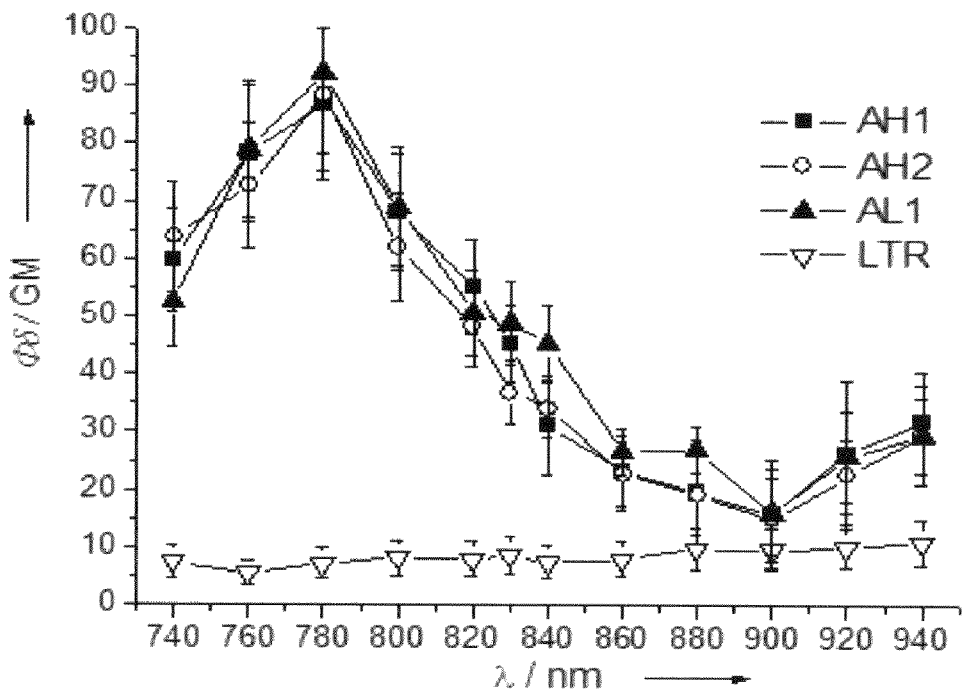
FIG. 13 shows two-photon action cross sections of the two-photon fluorescent probes according to the present invention, which were calculated based on the measured intensities of the two-photon induced fluorescence spectra of the probes in the wavelength range of 740-940 nm.

FIG. 13 shows two-photon action cross sections of the probes calculated based on the measured intensities of the two-photon induced fluorescence spectra of the probes in the wavelength range of 740-940 nm.

The graph shows that the probes AH1, AH2 and AD had the largest two-photon action cross section (>86 GM) at a wavelength of 780 nm, 9-fold larger than that of LYSOTRACKER™ Red (LTR) (~10 GM). These results clearly demonstrate that the probes AH1, AH2 and AL1 effectively stain acidic vesicles at a large penetration depth due to their large two-photon action cross sections so that the acidic vesicles can be excited to emit fluorescence.

As apparent from the foregoing, the two-photon fluorescent probes of the present invention can effectively bind to living cells and tissue under acidic conditions to produce two-photon excited fluorescence images with high intensity. Therefore, the two-photon fluorescent probes of the present invention can visualize acidic vesicles. In addition, the use of the two-photon fluorescent probes enables effective real-time monitoring of acidic vesicles.

What is claimed is:

1. A two-photon fluorescent probe for imaging acidic vesicles in live cells and tissue, represented by Formula 1:

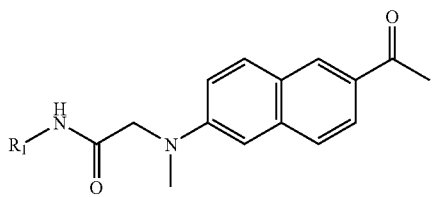

wherein $R_1$ is $(CH_3)_2NCH_2CH_2$— or

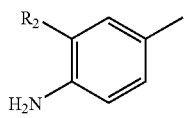

($R_2$ is a hydrogen atom or a methoxy group).

2. The two-photon fluorescent probe according to claim 1, wherein the probe is excited by light with a wavelength of 780 nm and has a two-photon action cross section ($\Phi\delta$) of at least 86 GM.

3. The two-photon fluorescent probe according to claim 1, wherein the probe shows two-photon emission spectra whose fluorescence intensity increases with decreasing pH of cells to be visualized.

4. The two-photon fluorescent probe according to claim 1, wherein the probe has a $pK_a$ of 4 to 5.

5. The two-photon fluorescent probe according to claim 1, wherein the probe has a water solubility of at least 5.0 μM.

6. The two-photon fluorescent probe according to claim 1, wherein the absorption spectra of the probe show bathochromic shifts with increasing solvent polarity.

7. The two-photon fluorescent probe according to claim 1, wherein the probe visualizes acidic vesicles at a penetration depth of 250 μm.

8. A method for imaging acidic vesicles in live cells and tissue, the method comprising introducing the probe according to claim 1 into cytosol to be visualized and observing two-photon excited fluorescence images emitted from the probe.

* * * * *